United States Patent [19]

Shuto et al.

[11] Patent Number: 5,262,441
[45] Date of Patent: Nov. 16, 1993

[54] AROMATIC COMPOUNDS, THEIR PRODUCTION PROCESSES AND THEIR COMPOSITIONS FOR THE CONTROL OF INSECT PESTS

[75] Inventors: Akira Shuto, Takarazuka; Noriyasu Sakamoto, Nishinomiya; Hirosi Kisida, Takarazuka; Hiroaki Fujimoto; Kimitoshi Umeda, both of Osaka; Noritada Matsuo, Itami, all of Japan

[73] Assignee: Sumitomo Chemical Company Limited, Osaka, Japan

[21] Appl. No.: 951,842

[22] Filed: Sep. 28, 1992

Related U.S. Application Data

[62] Division of Ser. No. 843,200, Feb. 28, 1992.

[30] Foreign Application Priority Data

Mar. 19, 1991 [JP] Japan .................. 3-081955

[51] Int. Cl.$^5$ .................. A01N 31/14; A01N 31/16; A01N 43/30; A01N 33/22
[52] U.S. Cl. .................. 514/718; 514/717; 514/712; 514/713; 514/716; 514/720; 514/721; 514/741; 514/742; 514/646; 514/657; 514/464
[58] Field of Search .............. 514/712, 713, 716, 717, 514/718, 720, 721, 741, 742, 464, 646, 657

[56] References Cited

U.S. PATENT DOCUMENTS

| | | |
|---|---|---|
| 4,048,235 | 9/1977 | Karrer ............... 260/612 R |
| 4,168,388 | 9/1979 | Lavagnino et al. ............. 568/645 |

FOREIGN PATENT DOCUMENTS

| | | |
|---|---|---|
| 0255935 | 4/1987 | European Pat. Off. . |
| 50-52036 | 5/1975 | Japan . |
| 57-176272 | 10/1982 | Japan . |

OTHER PUBLICATIONS

Lee et al, Chem. Abstracts: 99(13):100821f; "Analysis of Pesticide Residues by Chemical Derivitization", 1983.

Chemical Abstracts Formula Index, $C_{16}$-Z, vol. 99, part 2, 1983.

Lee et al., *J. Assoc. Off. Anal. Chem.*, vol. 66, No. 4, 1983, pp. 1029–1038.

*Primary Examiner*—Marianne M. Cintins
*Assistant Examiner*—Margaret Page
*Attorney, Agent, or Firm*—Birch, Stewart, Kolasch & Birch

[57] ABSTRACT

An aromatic compound of the formula:

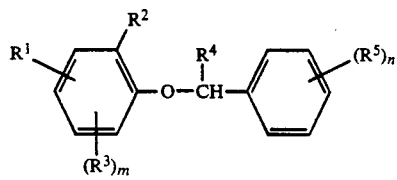

wherein $R^1$ is a $C_3$-$C_8$ alkyl group, a $C_3$-$C_8$ alkoxy group, an alkoxyalkyl group having 3 to 8 carbon atoms, a $C_3$-$C_8$ alkenyl group, a $C_3$-$C_8$ alkenyloxy group, an alkenyloxyalkyl group having 3 to 8 carbon atoms, a $C_3$-$C_8$ haloalkyl group, a $C_3$-$C_8$ alkoxy group, a haloalkoxyalkyl group having 3 to 8 carbon atoms, a $C_3$-$C_8$ haloalkenyl group, a $C_3$-$C_8$ haloalkenyloxy group, a haloalkenyloxyalkyl group having 3 to 8 carbon atoms or a $C_3$-$C_8$ alkynyloxy group; $R^2$ is a halogen atom; $R^3$ is, the same or different, a hydrogen atom, a halogen atom or a methyl group; $R^4$ is a hydrogen atom or a methyl group $R^5$ is, the same or different, a hydrogen atom, a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a 3,4-methylenedioxy group, a methoxymethyl group, a cyano group or a nitro group; m is an integer of 1 to 3; and n is an integer of 1 to 5. These compounds are useful for the control of insect pests.

8 Claims, No Drawings

5,262,441

AROMATIC COMPOUNDS, THEIR PRODUCTION PROCESSES AND THEIR COMPOSITIONS FOR THE CONTROL OF INSECT PESTS

This application is a division of copending application Ser. No. 07/843,200 pending, filed on Feb. 28, 1992, the entire contents of which are hereby incorporated by reference.

BACKGROUND OF THE INVENTION

1. Field of the Invention

The present invention relates to aromatic compounds, their production processes and their compositions for the control of insect pests.

2. Description of the Prior Art

It is described in U.S. Pat. Nos. 3,987,102, 4,094,989 and 4,153,731 that certain aromatic compounds are useful as insecticides and acaricides. But, their insecticidal and acaricidal activities are still not satisfactory.

SUMMARY OF THE INVENTION

As a result of the extensive study seeking aromatic compounds producing a satisfactory controlling effect on insect pests, it has been found that those of the following formula exhibit a remarkable juvenile hormone-like activity and can control significantly the growth of insect pests:

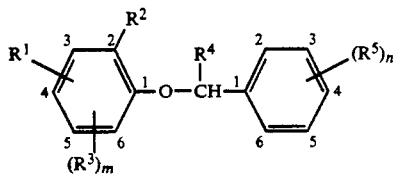

wherein $R^1$ is a $C_3-C_8$ alkyl group, a $C_3-C_8$ alkoxy group, an alkoxyalkyl group having 3 to 8 carbon atoms, a $C_3-C_8$ alkenyl group, a $C_3-C_8$ alkenyloxy group, an alkenyloxyalkyl group having 3 to 8 carbon atoms, a $C_3-C_8$ haloalkyl group, a $C_3-C_8$ haloalkoxy group, a haloalkoxyalkyl group having 3 to 8 carbon atoms, a $C_3-C_8$ haloalkenyl group, a $C_3-C_8$ haloalkenyloxy group, a haloalkenyloxyalkyl group having 3 to 8 carbon atoms or a $C_3-C_8$ alkynyloxy group; $R^2$ is a halogen atom; $R^3$ is, the same or different, a hydrogen atom, a halogen atom or a methyl group; $R^4$ is a hydrogen atom or a methyl group; $R^5$ is, the same or different, a hydrogen atom, a halogen atom, a $C_1-C_4$ alkyl group, a $C_1-C_4$ haloalkyl group, a $C_1-C_4$ alkoxy group, a $C_1-C_4$ haloalkoxy group, a $C_1-C_4$ alkylthio group, a $C_1-C_4$ haloalkylthio group, a 3,4-methylenedioxy group, a methoxymethyl group, a cyano group or a nitro group; m is an integer of 1 to 3; and n is an integer of 1 to 5. The present invention is based on the above finding.

DETAILED DESCRIPTION OF THE INVENTION

The aromatic compounds (I) of the invention have an excellent juvenile hormone-like activity against insect pests. They exhibit various actions such as metamorphosis inhibition, embryogenesis inhibition and sterilization and are thus efficacious as growth regulators, chemosterilants, ovicides or reproduction inhibitory agents on various insect pests such as agricultural, forestal, hygienic and stored grain insect pests. They are also efficacious against insect pests having an increased resistance to commercial insecticides.

In the formula (I) which represents the aromatic compounds of the invention, examples of the $C_3-C_8$ alkyl group represented by $R^1$ are n-propyl, isopropyl, n-butyl, sec-butyl, isobutyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, 1-methyl-1-propylbutyl, etc. Examples of the $C_3-C_8$ alkoxy group represented by $R^1$ are n-propoxy, isopropoxy, n-butoxy, sec-butoxy, isobutoxy, tert-butoxy, n-pentyloxy, neopentyloxy, 2-methylbutoxy, 1-methylbutoxy, 1-ethylpropoxy, 1,1-dimethylpropoxy, n-hexyloxy, 1-methylpentyloxy, 2-methylpentyloxy, 3-methylpentyloxy, 4-methylpentyloxy, 3,3-dimethylbutoxy, 2,2-dimethoxybutoxy, 1-1-dimethylbutoxy, 2-ethylbutoxy, 1-ethylbutoxy, 1,3-dimethylbutoxy, n-pentyloxy, 5-methylhexyloxy, 4-methylhexyloxy, 3-methylhexyloxy, 2-methylhexyloxy, 1-methylhexyloxy, 3-ethylpentyloxy, 2-ethylpentyloxy, 1-ethylpentyloxy, 4,4-dimethylpentyloxy, 3,3-dimethylpentyloxy, 2,2-dimethylpentyloxy, 1,1-dimethylpentyloxy, n-octyloxy, 6-methylheptyloxy, 5-methylheptyloxy, 4-methylheptyloxy, 3-methylheptyloxy, 2-methylheptyloxy, 1-methylheptyloxy, 1-ethylhexyloxy, 1-propylpentyloxy, 3-ethylhexyloxy, 5,5-dimethylhexyloxy, 4,4-dimethylhexyloxy, 2,2-diethylbutoxy, 3,3-diethylbutoxy, 1-methyl-1-propylbutoxy, etc. Examples of the alkoxyalkyl group having 3 to 8 carbon atoms represented by $R^1$ are ethoxymethyl, n-propoxymethyl, isopropoxymethyl, sec-butoxymethyl, isobutoxymethyl, (1-ethylpropoxy)methyl, (2-ethylpentyloxy)methyl, (1-ethylbutoxy)methyl, (2-ethylpentyloxy)methyl, (3-ethylpentyloxy)methyl, 2-methoxyethyl, 1-methoxyethyl, 2-ethoxyethyl, 3-methoxypropyl, 2-methoxypropyl, 1-methoxypropyl, 2-ethoxypropyl, 3-(n-propoxy)propyl, 4-methoxybutyl, 2-methoxybutyl, 4-ethoxybutyl, 2-ethoxybutyl, 5-ethoxypentyl, 6-ethoxyhexyl, etc. Examples of the $C_3-C_8$ alkenyl group represented by $R^1$ include 1-methylvinyl, allyl, 2-methylallyl, 1-propenyl, 1-methyl-1-propenyl, 2-methyl-1-propenyl, 1,1-dimethyl-2-propenyl, 2-butenyl, 3-butenyl, 3-methyl-2-butenyl, 2-methyl-2-butenyl, 2-methyl-3-butenyl, 1-pentenyl, 2-pentenyl, 1-hexenyl, 2-hexenyl, 5-hexenyl, 6-heptenyl, 7-octenyl, etc. Examples of the $C_3-C_8$ alkenyloxy group represented by $R^1$ are allyloxy, 2-methylallyloxy, 1-propenyloxy, 2-methyl-1-propenyloxy, 2-butenyloxy, 3-butenyloxy, 3-methyl-2-butenyloxy, 2-methyl-2-butenyloxy, 2-methyl-3-butenyloxy, 2-pentenyloxy, 1-pentenyloxy, 1-hexenyloxy, 2-hexenyloxy, 5-hexenyloxy, 6-heptenyloxy, 7-octenyloxy, etc. Examples of the alkenyloxyalkyl group having 3 to 8 carbon atoms represented by $R^1$ are allyloxymethyl, (2-methylallyloxy)methyl, (1-propenyloxy)methyl, (2-methyl-1-propenyloxy)methyl, (2-butenyloxy)methyl, (3-butenyloxy)methyl, (3-methyl-2-butenyloxy)methyl, (2-methyl-2-butenyloxy)- methyl, (2-methyl-3-butenyloxy)methyl, (2-pentenyloxy)methyl, (1-pentenyloxy)methyl, (1-hexenyloxy)methyl, (2-hexenyloxy)methyl, (5-hexenyloxy)methyl, (6-heptenyloxy)methyl, 2-allyloxyethyl, 2-(2-methylallyloxy)ethyl, 2-(1-propenyloxy)ethyl, 2-(2-methyl-1-propenyloxy)ethyl, 2-(2-butenyloxy)ethyl, 2-(3-butenyloxy)ethyl, 2-(3-methyl-2-butenyloxy)ethyl, 2-(2-methyl-2-butenyloxy)ethyl, 2-(2-methyl-3-butenyloxy)ethyl, 2-(2-pentenyloxy)ethyl, 2-(1-pentenyloxy)ethyl, 2-(1-hexenyloxy)ethyl, 2-(2-hexenyloxy)ethyl, 2-(5-hexenyloxy)ethyl, 1-allyloxyethyl, 1-(2-methylallyloxy)ethyl, 1-(1-propenyloxy)ethyl, 1-(2-methyl-1-propenyloxy)ethyl, 1-(2-butenyloxy)ethyl, 1-(3-butenyloxyethyl, 1-(3-methyl-2-butenyloxy)ethyl, 1-(2-methyl-2-butenyloxy)ethyl, 1-(2-methyl-3-butenyloxy)ethyl, 1-(2-pentenyloxy)ethyl, 1-(1-pentenyloxy)ethyl, 1-(1-hexenyloxy)ethyl, 1-(2-hexenyloxy)ethyl 1-(5-hexenyloxy)ethyl, etc. Examples of the $C_3$–$C_8$ haloalkyl group represented by $R^1$ are 3-fluoropropyl, 2,2,3,3,3-pentafluoropropyl, 2-chloro-1-methylpropyl, 3-chloropropyl, 2-chloropropyl, 2,3-dichloropropyl, 3-bromopropyl, 2-bromopropyl, 3-iodopropyl, 4-fluorobutyl, 3,3,4,4,4-pentafluoro-2-butyl, 4-chlorobutyl, 3-chlorobutyl, 2,3,4-trichlorobutyl, 4-bromobutyl, 3-bromobutyl, 4-iodobutyl, 5-fluoropentyl, 5-chloropentyl, 5-bromopentyl, 6-fluorohexyl, 6-chlorohexyl, 6-bromohexyl, 7-fluoroheptyl, 7-bromoheptyl, 8-fluorooctyl, 8-bromooctyl, etc. Examples of the $C_3$–$C_8$ haloalkoxy group represented by $R^1$ are 3-fluoropropoxyl, 2,2,3,3,3-pentafluoropropoxy, 2-chloro-1-methylpropoxy, 3-chloropropoxy, 2-chloropropoxy, 2,3-dichloropropoxy, 3-bromopropoxy, 2-bromopropoxy, 3-iodopropoxy, 4-fluorobutoxy, 3,3,4,4,4-pentafluoro-2-butoxy, 4-chlorobutoxy, 3-chlorobutoxy, 2,3,4-trichlorobutoxy, 4-bromobutoxy, 3-bromobutoxy, 4-iodobutoxy, 5-fluoropentyloxy, 5-chloropentyloxy, 5-bromopentyloxy, 6-fluorohexyloxy, 6-chlorohexyloxy, 6-bromohexyloxy, 7-fluoroheptyloxy, 7-bromoheptyloxy, 8-fluorooctyloxy, 8-bromooctyloxy, etc. Examples of the haloalkoxyalkyl group having 3 to 8 carbon atoms represented by $R^1$ are (3-fluoropropoxy)methyl, (2,2,3,3,3-pentafluoropropoxy)methyl, (2-chloro-1-methylpropoxy)methyl, (3-chloropropoxy)methyl, (2-chloropropoxy)methyl, (2,3-dichloropropoxy)methyl, (3-bromopropoxy)methyl, (2-bromopropoxy)methyl, (3-iodopropoxy)methyl, (4-fluorobutoxy)methyl, (3,3,4,4,4-pentafluoro-2-butoxy)methyl, (4-chlorobutoxy)methyl, (3-chlorobutoxy)methyl, (2,3,4-trichlorobutoxy)methyl, (4-bromobutoxy)methyl, (3-bromobutoxy)methyl, (4-iodobutoxy)methyl, (5-fluoropentyloxy)methyl, (5-chloropentyloxy)methyl, (5-bromopentyloxy)methyl, (6-fluorohexyloxy)methyl, (6-chlorohexyloxy)methyl, (6-bromohexyloxy)methyl, (7-fluoroheptyloxy)methyl, (7-bromoheptyloxy)methyl, 1-(3-fluoropropoxy)ethyl, 1-(2,2,3,3,3-pentafluoropropoxy)ethyl, 1-(2-chloro-1-methylpropoxy)ethyl, 1-(3-chloropropoxy)ethyl, 1-(2-chloropropoxy)ethyl, 1-(2,3-dichloropropoxy)ethyl, 1-(3-bromopropoxy)ethyl, 1-(2-bromopropoxy)ethyl, 1-(3-iodopropoxy)ethyl, 1-(4-fluorobutoxy)ethyl, 1-(3,3,4,4,4-pentafluoro-2-butoxy)ethyl, 1-(4-chlorobutoxy)ethyl, 1-(3-chlorobutoxy)ethyl, 1-(2,3,4-trichlorobutoxy)ethyl, 1-(4-bromobutoxy)ethyl, 1-(3-bromobutoxy)ethyl, 1-(4-iodobutoxy)ethyl, 1-(5-fluoropentyloxy)ethyl, 1-(5-chloropentyloxy)ethyl, 1-(5-bromopentyloxy)ethyl, 1-(6-fluorohexyloxy)ethyl, 1-(6-chlorohexyloxy)ethyl, 1-(6-bromohexyloxy)ethyl, 2-(3-fluoropropoxy)ethyl, 2-(2,2,3,3,3-pentafluoropropoxy)ethyl, 2-(2-chloro-1-methylpropoxy)ethyl, 2-(3-chloropropoxy)ethyl, 2-(2-chloropropoxy)ethyl, 2-(2,3-dichloropropoxy)ethyl, 2-(3-bromopropoxy)ethyl, 2-(2-bromopropoxy)ethyl, 2-(3-iodopropoxy)ethyl, 2-(4-fluorobutoxy)ethyl, 2-(3,3,4,4,4-pentafluoro-2-butoxy)ethyl, 2-(4-chlorobutoxy)ethyl, 2-(3-chlorobutoxy)ethyl, 2-(2,3,4-trichlorobutoxy)ethyl, 2-(4-bromobutoxy)ethyl, 2-(3-bromobutoxy)ethyl, 2-(4-iodobutoxy)ethyl, 2-(5-fluoropentyloxy)ethyl, 2-(5-chloropentyloxy)ethyl, 2-(5-bromopentyloxy)ethyl, 2-(6-fluorohexyloxy)ethyl, 2-(6-chlorohexyloxy)ethyl, 2-(6-bromohexyloxy)ethyl, etc. Examples of the $C_3$–$C_8$ haloalkenyl group represented by $R^1$ include 2,3-dichloroallyl, 2,3-dibromoallyl, 2-chloro-2-propenyl, 3-chloro-2-propenyl, 2-bromo-2-propenyl, 2-chloromethyl-2-propenyl, 2-chloro-3-butenyl, 3-chloro-2-butenyl, 4-chloro-2-butenyl, 4-bromo-2-butenyl, 7-chloro-7-octenyl, etc. Examples of the $C_3$–$C_8$ haloalkenyloxy group represented by $R^1$ are 2,3-dichloroallyloxy, 2,3-dibromoallyloxy, 2-chloro-2-propenyloxy, 3-chloro-2-propenyloxy, 2-bromo-2-propenyloxy, 2-chloro-3-butenyloxy, 3-chloro-2-butenyloxy, 4-chloro-2-butenyloxy, 4-bromo-2-butenyloxy, 7-chloro-7-octenyloxy, etc. Examples of the haloalkenyloxyalky group having 3 to 8 carbon atoms represented by $R^1$ are (2,3-dichloroallyloxy)methyl, (2,3-dibromoallyloxy)methyl, (2-chloro-2-propenyloxy)methyl, (3-chloro-2-propenyloxy)methyl, (2-bromo-2-propenyloxy)methyl, (2-chloro-3-butenyloxy)methyl, (3-chloro-2-butenyloxy)methyl, (4-chloro-2-butenyloxy)methyl, (4-bromo-2-butenyloxy)methyl, (7-chloro-7-octenyloxy)methyl, 1-(2,3-dichloroallyloxy)ethyl, 1-(2,3-dibromoallyloxy)ethyl, 1-(2-chloro-2-propenyloxy)ethyl, 1-(3-chloro-2-propenyloxy)ethyl, 1-(2-bromo-2-propenyloxy)ethyl, 1-(2-chloro-3-butenyloxy)ethyl, 1-(3-chloro-2-butenyloxy)ethyl, 1-(4-chloro-2-butenyloxy)ethyl, 1-(4-bromo-2-butenyloxy)ethyl, 1-(7-chloro-7-octenyloxy)ethyl, 2-(2,3-dichloroallyloxy)ethyl, 2-(2,3-dibromoallyloxy)ethyl, 2-(2-chloro-2-propenyloxy)ethyl, 2-(3-chloro-2-propenyloxy)ethyl, 2-(2-bromo-2-propenyloxy)ethyl, 2-(2-chloro-3-butenyloxy)ethyl, 2-(3-chloro-2-butenyloxy)ethyl, 2-(4-chloro-2-butenyloxy)ethyl, 2-(4-bromo-2-butenyloxy)ethyl, 2-(7-chloro-7-octenyloxy)ethyl, etc. Examples of the $C_3$–$C_8$ alkynyloxy group represented by $R^1$ are 2-propynyloxy, 1-methyl-2-propynyloxy, 1-ethyl-2-propynyloxy, 1-propyl-2-propynyloxy, 2-butynyloxy, 1-ethyl-2-butynyloxy, 1-propyl-2-butynyloxy, 1-n-butyl-2-butynyloxy, 2-pentynyloxy, 4-methyl-2-pentynyloxy, 1,4-dimethyl-2-pentynyloxy, 1-ethyl-4-methyl-2-pentynyloxy, 2-hexynyloxy, 3-hexynyloxy, 2-heptynyloxy, 2-octynyloxy, 7-octynyloxy, etc. Examples of the halogen atom represented by $R^2$, $R^3$ and $R^5$ are fluorine, chlorine, bromine and iodine, etc., among which preferred is chlorine. Examples of the $C_1$–$C_4$ alkyl group represented by $R^5$ are methyl, ethyl, n-propyl, isopropyl, n-butyl, sec-butyl, isobutyl, tert-butyl, etc., among which preferred is ethyl. Examples of the $C_1$–$C_4$ haloalkyl group represented by $R^5$ include trifluoromethyl, difluoromethyl, 2-fluoroethyl, 1-fluoroethyl, 1,2-difluoroethyl, 2,2,2-trifluoroethyl, 2-chloroethyl, 3-fluoro-n-propyl, 2-fluoro-n-propyl, 1-fluoro-n-propyl, 3-chloro-n-propyl, 3-bromo-n-propyl, 4-fluoro-n-butyl, 4-chloro-n-butyl, etc. Examples of the $C_1$–$C_4$ alkoxy group represented by $R^5$ are methoxy, ethoxy, propoxy, isopropoxy, n-butoxy, tert-butoxy, isobutoxy, sec-butoxy, etc. Example of the $C_1$–$C_4$ haloalkoxy group include trifluoromethoxy, difluoromethoxy, bromodifluoromethoxy, chlorodifluoromethoxy, 2-fluoroethoxy, 2,2,2-trifluoroethoxy, perfluoroethoxy, 1,1,2-trifluoroethoxy, 1-fluoroethoxy, 1,2-difluoroethoxy, 2-chloro-1,1,2-trifluoroethoxy, 3-fluoro-n-propoxy, 1-fluoro-n-propoxy, 2-fluoro-n-propoxy, perfluoro-n-propoxy, 4-fluoro-n-butoxy, 2-chloroethoxy, 3-chloro-n-propoxy, 4-chloro-n-butoxy, 3-bromo-n-propoxy, 1,1,2,2-tetrafluoroethoxy, 1,1-difluoromethoxy, etc. Examples of the $C_1$-$C_4$ alkylthio group represented by $R^5$ are methylthio, ethylthio, n-propylthio, isopropylthio, n-butylthio, isobutylthio, sec-butylthio, tert-butylthio, etc. Examples of the $C_1$-$C_4$ haloalkylthio group represented by $R^5$ are difluoromethylthio, trifluoromethylthio, 2-fluoroethylthio, 1-fluoroethylthio, 2-chloroethylthio, 1,2-difluoroethylthio, 2,2,2-trifluoroethylthio, 3-fluoropropylthio, 2-fluoropropylthio, 1-fluoropropylthio, 3-chloropropylthio, 3-bromopropylthio, 4-fluorobutylthio, 4-chlorobutylthio, etc. Futher, $(R^5)_n$ is preferably present at the 4-position.

The aromatic compounds (I) of the invention can be produced by various processes, among which typical examples are shown below.

Process A

The aromatic compound (I) is produced by reacting a phenol compound of the formula:

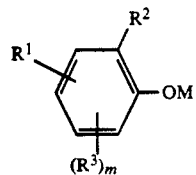

wherein M is an alkali metal atom or a hydrogen atom and $R^1$, $R^2$, $R^3$ and m are each as defined above with a halide of the formula:

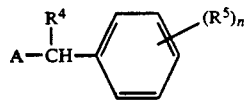

wherein A is a halogen atom and $R^4$, $R^5$ and n are each as defined above.

The reaction may be carried out usually in an inert solvent in the presence of a base at a temperature of from about −20° C. to the boiling point of the solvent, preferably from about −5° C. to the boiling point of the solvent. When the phenol compound (II) is employed in a metal salt form, the base is not necessarily required to use.

The molar proportion of the phenol compound (II) and the halide (III) to be used for the reaction is not limitative but is preferred to be nearly equal. Examples of the inert solvent are lower alcohols (e.g. methanol, ethanol, propanol, isopropanol, tert-butyl alcohol), ketones (e.g. acetone, methyl ethyl ketone), hydrocarbons (e.g. hexane, benzene, toluene), ethers (e.g. diethyl ether, diisopropyl ether, tetrahydrofuran, dioxane), acid amines (e.g. N,N-dimethylformamide, hexamethylphosphoric triamide), halogenated hydrocarbons (e.g. dichloromethane, chloroform, 1,2-dichloroethane, chlorobenzene), nitriles (e.g. acetonitrile), nitro compounds (e.g. nitromethane), dimethyl sulfoxide, sulfolane, water and mixtures thereof. Example of the base are alkali metal hydroxides (e.g. sodium hydroxide, potassium hydroxide), alkali metal carbonates (e.g. sodium carbonate, potassium carbonate), alkali metals (e.g. metallic sodium), alkali metal hydrides (e.g. sodium hydride), organic bases (e.g. sodium methoxide, sodium ethoxide, triethylamine, pyridine), etc. When necessary or desired, an ammonium salt such as triethylbenzylammonium chloride and tetrabutylammonium bromide may be added to the reaction system as a catalyst.

After completion of the reaction, post-treatment may follow in a per se conventional manner such as extraction with an organic solvent and concentration. When necessary or desired, the product may further be purified by chromatography, distillation, recrystallization, etc.

Process B

The aromatic compound (I) is produced by reacting a phenol compound of the formula:

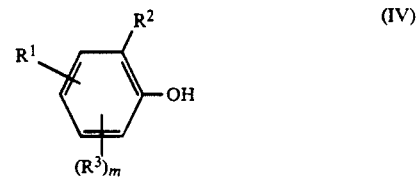

wherein $R^1$, $R^2$, $R^3$ and m are each as defined above with an alcohol of the formula:

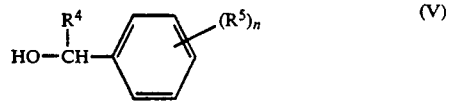

wherein $R^4$, $R^5$ and n are each as defined above. This process is advantageously applicable when $R^4$ is other than a hydrogen atom.

The reaction may be carried out normally in an inert solvent in the presence of a dehydrating catalyst or agent at a temperature of from about −20° to 200° C. or the boiling point of the inert solvent.

The molar proportion of the phenol compound (IV) and the alcohol (V) is not limitative but is preferred to be nearly equal. Examples of the dehydrating catalyst are inorganic acids (e.g. hydrochloric acid, sulfuric acid), aromatic sulfonic acids, sulfonic acid halides, etc. Examples of the dehydrating agent include dicyclohexylcarbodiimide, diisopropyl azodicarboxylate with triphenylphosphine, diethyl azodicarboxylate with triphenylphosphine, etc. Examples of the inert solvent are hydrocarbons (e.g. benzene, toluene, xylene), ethers (e.g. diethyl ether, diisopropyl ether, tetrahydrofuran, dioxane), halogenated hydrocarbons (e.g. carbon tetrachloride, dichloromethane, 1,2-dichloroethane, chlorobenzene, dichlorobenzene), etc.

After completion of the reaction, post-treatment may follow in a per se conventional manner such as extraction with an organic solvent and concentration. When necessary or desired, the product may further be purified by chromotography, distillation, recrystallization, etc.

The aromatic compounds (I) of the invention have some asymmetric carbon atoms and can form optical isomers. Those optical isomers and their mixtures fall within the scope of the invention.

Among the starting compounds in the above processes, the halide (III) and the alcohol (V) are available on the commercial market or can be readily produced from appropriate commercial products by the known method as described in Chem. Ber., 89, 1732 (1956), J. Amer. Chem. Soc., 76, 908 (1954), etc.

Among the starting compounds in the above processes, the phenol compound (II) wherein M is an alkali metal atom can be prepared from the corresponding phenol compound (IV) (i.e. the compound of the formula(II) wherein M is a hydrogen atom).

The phenol compound (IV) are available on the commercial market or can be readily produced from appropriate commercial products by conventional method.

The phenol compound (II) or (IV) wherein $R^2$ is a chlorine atom can be also prepared by the known method as described in J. Amer. Chem. Soc., 73, 2723 (1951), J. Org. Chem., 39, 1160(1974), etc. Furthermore, the phenol compound (IV) may be prepared by reacting the corresponding non-clorinated compound, i.e. a phenol compound, of the formula:

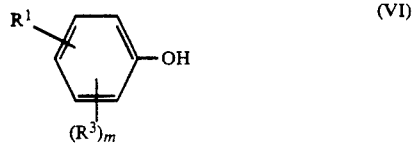

(VI)

wherein $R^1$, $R^3$ and m are each as defined above with a chlorinating agent, preferably in an inert solvent.

The molar proportion of the phenol compound (VI) and the chlorinating agent is not limitative but it is ordinary to use the chlorinating agent in an amount equivalent to the phenol compound (VI) or somewhat in excess. Examples of the chlorinating agent are chlorine, tert-butyl hypochlorite, sulfuryl chloride, etc. If necessary and desired, the reaction can be carried out in the presence of an inert solvent. Examples of the solvent are dichloromethane, 1,2-dichloroethane, carbon tetrachloride, benzene, acetic acid, etc. The chlorinating agent itself may be available as a reaction medium when it is liquid. The reaction temperature is usually from about $-80°$ C. to the refluxing temperature of the reaction system, preferably from about $-20°$ C. to the refluxing temperature of the reaction system.

After completion of the reaction, post-treatment may follow in a per se conventional manner such as extraction with an organic solvent and concentration. When necessary or desired, the product may further be purified by chromatography, distillation, recrystallization, etc.

Examples of the aromatic compounds (I) of the present invention are shown in Table 1.

TABLE 1

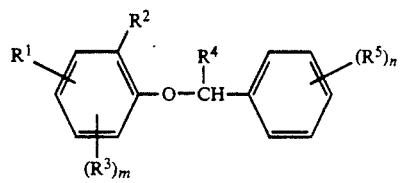

| $R^1$ | $R^2$ | $(R^3)_m$ | $R^4$ | $(R^5)_n$ |
|---|---|---|---|---|
| 4-O-sec-$C_4H_9$ | Cl | H | H | 4-Cl |
| 4-O-sec-$C_4H_9$ | Cl | H | H | 4-Br |
| 4-O-sec-$C_4H_9$ | Cl | H | H | 4-F |
| 4-O-sec-$C_4H_9$ | Cl | H | H | 3,4-$F_2$ |
| 4-O-sec-$C_4H_9$ | Cl | H | H | 4-I |
| 4-O-sec-$C_4H_9$ | Cl | H | H | 3,4-$Cl_2$ |
| 4-O-sec-$C_4H_9$ | Cl | H | H | 2,3,4,5,6-$F_5$ |
| 4-O-sec-$C_4H_9$ | Cl | H | H | 3,5-$F_2$ |
| 4-O-sec-$C_4H_9$ | Cl | H | H | 4-$CH_3$ |
| 4-O-sec-$C_4H_9$ | Cl | H | H | 4-$C_2H_5$ |
| 4-O-sec-$C_4H_9$ | Cl | H | H | 4-n-$C_3H_7$ |
| 4-O-sec-$C_4H_9$ | Cl | H | H | 4-iso-$C_3H_7$ |
| 4-O-sec-$C_4H_9$ | Cl | H | H | 4-n-$C_4H_9$ |
| 4-O-sec-$C_4H_9$ | Cl | H | H | 4-sec-$C_4H_9$ |
| 4-O-sec-$C_4H_9$ | Cl | H | H | 4-tert-$C_4H_9$ |
| 4-O-sec-$C_4H_9$ | Cl | H | H | 4-iso-$C_4H_9$ |
| 4-O-sec-$C_4H_9$ | Cl | H | H | 4-$OCH_3$ |
| 4-O-sec-$C_4H_9$ | Cl | H | H | 4-$OC_2H_5$ |
| 4-O-sec-$C_4H_9$ | Cl | H | H | 4-O-n-$C_3H_7$ |
| 4-O-sec-$C_4H_9$ | Cl | H | H | 4-O-iso-$C_3H_7$ |
| 4-O-sec-$C_4H_9$ | Cl | H | H | 4-O-n-$C_4H_9$ |
| 4-O-sec-$C_4H_9$ | Cl | H | H | 4-O-sec-$C_4H_9$ |
| 4-O-sec-$C_4H_9$ | Cl | H | H | 4-O-tert-$C_4H_9$ |
| 4-O-sec-$C_4H_9$ | Cl | H | H | 4-$CH_2CH_2F$ |
| 4-O-sec-$C_4H_9$ | Cl | H | H | 4-$CF_3$ |
| 4-O-sec-$C_4H_9$ | Cl | H | H | 4-$CF_2H$ |
| 4-O-sec-$C_4H_9$ | Cl | H | H | 4-$CF_2CF_3$ |
| 4-O-sec-$C_4H_9$ | Cl | H | H | 4-$CHFCH_2F$ |
| 4-O-sec-$C_4H_9$ | Cl | H | H | 4-$(CH_2)_3F$ |
| 4-O-sec-$C_4H_9$ | Cl | H | H | 4-$(CH_2)_4F$ |
| 4-O-sec-$C_4H_9$ | Cl | H | H | 4-$OCF_2H$ |
| 4-O-sec-$C_4H_9$ | Cl | H | H | 4-$OCF_2CF_2H$ |
| 4-O-sec-$C_4H_9$ | Cl | H | H | 4-$SCF_2H$ |
| 4-O-sec-$C_4H_9$ | Cl | H | H | 4-$SCF_2CF_2H$ |
| 4-O-sec-$C_4H_9$ | Cl | H | H | 4-$SCH_3$ |

TABLE 1-continued

Structure: R¹-substituted phenyl with R² ortho, (R³)ₘ, connected via O-CHR⁴ to phenyl with (R⁵)ₙ

| R¹ | R² | (R³)ₘ | R⁴ | (R⁵)ₙ |
|---|---|---|---|---|
| 4-O-sec-$C_4H_9$ | Cl | H | H | 4-S$C_2H_5$ |
| 4-O-sec-$C_4H_9$ | Cl | H | H | 4-S-n-$C_3H_7$ |
| 4-O-sec-$C_4H_9$ | Cl | H | H | 4-S-iso-$C_3H_7$ |
| 4-O-sec-$C_4H_9$ | Cl | H | H | 4-S-n-$C_4H_9$ |
| 4-O-sec-$C_4H_9$ | Cl | H | H | 4-S-sec-$C_4H_9$ |
| 4-O-sec-$C_4H_9$ | Cl | H | H | 3,4-O$CH_2$O— |
| 4-O-sec-$C_4H_9$ | Cl | H | H | 4-$CH_2OCH_3$ |
| 4-O-sec-$C_4H_9$ | Cl | H | H | 4-CN |
| 4-O-sec-$C_4H_9$ | Cl | H | H | 4-$NO_2$ |
| 4-O-sec-$C_4H_9$ | Cl | H | H | 2,4-$(CH_3)_2$ |
| 4-O-sec-$C_4H_9$ | Cl | H | H | 2,5-$(CH_3)_2$ |
| 4-O-sec-$C_4H_9$ | Cl | H | H | 3,4-$(CH_3)_2$ |
| 4-O-sec-$C_4H_9$ | Cl | H | H | 3,5-$(CH_3)_2$ |
| 4-O-sec-$C_4H_9$ | Cl | H | H | H |
| 4-O-sec-$C_4H_9$ | Cl | H | H | 2-$CH_3$ |
| 4-O-sec-$C_4H_9$ | Cl | H | H | 3-$CH_3$ |
| 4-O-sec-$C_4H_9$ | Cl | H | H | 4-$C_2H_5$ |
| 4-O-sec-$C_4H_9$ | Br | H | H | 4-Cl |
| 4-O-sec-$C_4H_9$ | F | H | H | 4-Cl |
| 4-O-sec-$C_4H_9$ | I | H | H | 4-Cl |
| 4-O-sec-$C_4H_9$ | Cl | 5-Cl | H | 4-Cl |
| 4-O-sec-$C_4H_9$ | Cl | 3-Cl | H | 4-Cl |
| 4-O-sec-$C_4H_9$ | Cl | H | $CH_3$ | 4-Cl |
| 4-O-sec-$C_4H_9$ | Cl | 5-F | H | 4-Cl |
| 4-O-sec-$C_4H_9$ | Cl | 5-F | H | 4-$C_2H_5$ |
| 4-O-sec-$C_4H_9$ | Cl | 5-$CH_3$ | H | 4-Cl |
| 4-O-sec-$C_4H_9$ | Cl | 5-$CH_3$ | H | 4-$C_2H_5$ |
| 4-O-sec-$C_4H_9$ | Cl | 3,5-$F_2$ | H | 4-Cl |
| 4-O-sec-$C_4H_9$ | Cl | 3,5-$F_2$ | H | 4-$C_2H_5$ |
| 4-O-sec-$C_4H_9$ | Cl | 3,5-$Cl_2$ | H | 4-Cl |
| 4-O-sec-$C_4H_9$ | Cl | 3,5-$Cl_2$ | H | 4-$C_2H_5$ |
| 4-$CH_2CH(C_2H_5)_2$ | Cl | H | H | 4-Cl |
| 4-$CH_2CH(C_2H_5)_2$ | Cl | H | H | 4-$C_2H_5$ |
| 4-$CH_2OCH_2CH(CH_3)_2$ | Cl | H | H | 4-Cl |
| 4-$CH_2OCH_2CH(CH_3)_2$ | Cl | H | H | 4-$C_2H_5$ |
| 4-$OCH_2C(CH_3)=CH_2$ | Cl | H | H | 4-Cl |
| 4-$OCH_2CH=CH_2$ | Cl | H | H | 4-Cl |
| 4-$OCH_2CH=CH_2$ | Cl | H | H | 4-$C_2H_5$ |
| 4-$OCH_2CH=CH(CH_3)$ | Cl | H | H | 4-Cl |
| 4-$O(CH_2)_3Cl$ | Cl | H | H | 4-Cl |
| 4-$O(CH_2)_3Cl$ | Cl | H | H | 4-$C_2H_5$ |
| 4-$O(CH_2)_3Br$ | Cl | H | H | 4-Cl |
| 4-$O(CH_2)_3Br$ | Cl | H | H | 4-$C_2H_5$ |
| 4-$OCH_2C\equiv CH$ | Cl | H | H | 4-Cl |
| 4-$OCH_2C\equiv CH$ | Cl | H | H | 4-$C_2H_5$ |
| 4-$OCH_2C\equiv CCH_3$ | Cl | H | H | 4-Cl |
| 4-$OCH(C_2H_5)_2$ | Cl | H | $CH_3$ | 4-Cl |
| 4-$OCH(C_2H_5)_2$ | Cl | H | $CH_3$ | 4-$C_2H_5$ |
| 4-$(CH_2)_3CH(CH_3)_2$ | Cl | H | H | 4-Cl |
| 4-$(CH_2)_3CH(CH_3)_2$ | Cl | H | H | 4-$C_2H_5$ |
| 4-sec-$C_4H_9$ | Cl | H | H | 4-Cl |
| 4-sec-$C_4H_9$ | Cl | H | H | 4-$C_2H_5$ |
| 4-$C(CH_3)_2C_2H_5$ | Cl | H | H | 4-Cl |
| 4-$C_6H_{13}$ | Cl | H | H | 4-Cl |
| 4-$CH(CH_3)(CH_2)_4H$ | Cl | H | H | 4-Cl |
| 4-$CH_2CH(CH_3)(CH_2)_3H$ | Cl | H | H | 4-Cl |
| 4-$C_2H_4CH(CH_3)C_2H_5$ | Cl | H | H | 4-Cl |
| 4-$(CH_2)_3CH(CH_3)_2$ | Cl | H | H | 4-Cl |
| 4-$C_2H_4C(CH_3)_3$ | Cl | H | H | 4-Cl |
| 4-$C_2H_4C(CH_3)_3$ | Cl | H | H | 4-$C_2H_5$ |
| 4-$C(CH_3)_2C_3H_7$ | Cl | H | H | 4-Cl |
| 4-$C(CH_3)_2C_3H_7$ | Cl | H | H | 4-$C_2H_5$ |
| 4-$CH_2C(CH_3)_2C_2H_5$ | Cl | H | H | 4-Cl |
| 4-$CH_2CH(C_2H_5)_2$ | Cl | H | H | 4-Cl |
| 4-$CH(C_2H_5)C_3H_7$ | Cl | H | H | 4-Cl |
| 4-$CH(CH_3)CH_2CH(CH_3)_2$ | Cl | H | H | 4-Cl |
| 4-$C_7H_{15}$ | Cl | H | H | 4-Cl |
| 4-$(CH_2)_4CH(CH_3)_2$ | Cl | H | H | 4-Cl |
| 4-$(CH_2)_3CH(CH_3)C_2H_5$ | Cl | H | H | 4-Cl |
| 4-$C_2H_4CH(CH_3)C_3H_7$ | Cl | H | H | 4-Cl |
| 4-$CH_2CH(CH_3)C_4H_9$ | Cl | H | H | 4-Cl |

TABLE 1-continued

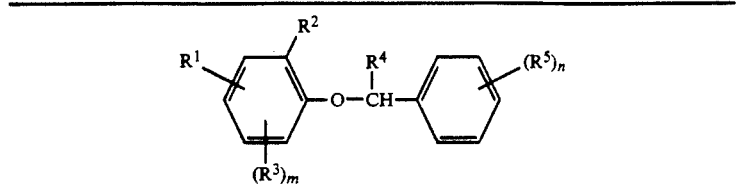

| R¹ | R² | (R³)ₘ | R⁴ | (R⁵)ₙ |
|---|---|---|---|---|
| 4-CH₂CH(CH₃)C₄H₉ | Cl | H | H | 4-C₂H₅ |
| 4-CH(CH₃)C₅H₁₁ | Cl | H | H | 4-Cl |
| 4-CH(CH₃)C₅H₁₁ | Cl | H | H | 4-C₂H₅ |
| 4-C₂H₄CH(C₂H₅)₂ | Cl | H | H | 4-Cl |
| 4-CH₂CH(C₂H₅)C₃H₇ | Cl | H | H | 4-Cl |
| 4-CH(C₂H₅)C₄H₉ | Cl | H | H | 4-Cl |
| 4-CH(C₂H₅)C₄H₉ | Cl | H | H | 4-C₂H₅ |
| 4-(CH₂)₂C(CH₃)₃ | Cl | H | H | 4-Cl |
| 4-C₂H₄C(CH₃)₂C₂H₅ | Cl | H | H | 4-Cl |
| 4-CH₂C(CH₃)₂C₃H₇ | Cl | H | H | 4-Cl |
| 4-C(CH₃)₂C₄H₉ | Cl | H | H | 4-Cl |
| 4-(CH₂)₅CH(CH₃)₂ | Cl | H | H | 4-Cl |
| 4-(CH₂)₅CH(CH₃)₂ | Cl | H | H | 4-C₂H₅ |
| 4-(CH₂)₄CH(CH₃)C₂H₅ | Cl | H | H | 4-Cl |
| 4-(CH₂)₃CH(CH₃)C₃H₇ | Cl | H | H | 4-Cl |
| 4-(CH₂)₃CH(CH₃)C₃H₇ | Cl | H | H | 4-C₂H₅ |
| 4-C₂H₄CH(CH₃)C₄H₉ | Cl | H | H | 4-Cl |
| 4-CH₂CH(CH₃)C₅H₁₁ | Cl | H | H | 4-Cl |
| 4-CH(CH₃)C₆H₁₃ | Cl | H | H | 4-Cl |
| 4-CH(CH₃)C₆H₁₃ | Cl | H | H | 4-C₂H₅ |
| 4-CH(C₂H₅)C₅H₁₁ | Cl | H | H | 4-Cl |
| 4-CH(C₂H₅)C₅H₁₁ | Cl | H | H | 4-C₂H₅ |
| 4-C₈H₁₇ | Cl | H | H | 4-Cl |
| 4-C₈H₁₇ | Cl | H | H | 4-C₂H₅ |
| 4-(CH₂)₄C(CH₃)₃ | Cl | H | H | 4-Cl |
| 4-(CH₂)₃C(CH₃)₂C₂H₅ | Cl | H | H | 4-Cl |
| 4-CH₂C(C₂H₅)₃ | Cl | H | H | 4-Cl |
| 4-C₂H₄C(C₂H₅)₂CH₃ | Cl | H | H | 4-Cl |
| 4-OC₃H₇ | Cl | H | H | 4-Cl |
| 4-OC₃H₇ | Cl | H | H | 4-C₂H₅ |
| 4-OC₄H₉ | Cl | H | H | 4-Cl |
| 4-O-iso-C₄H₉ | Cl | H | H | 4-Cl |
| 4-O-iso-C₄H₉ | Cl | H | H | 4-C₂H₅ |
| 4-O-tert-C₄H₉ | Cl | H | H | 4-Cl |
| 4-OC₈H₁₇ | Cl | H | H | 4-Cl |
| 4-OC₈H₁₇ | Cl | H | H | 4-C₂H₅ |
| 4-OCH₂CH(CH₃)C₂H₅ | Cl | H | H | 4-Cl |
| 4-OCH(CH₃)C₃H₇ | Cl | H | H | 4-Cl |
| 4-OCH(CH₃)C₃H₇ | Cl | H | H | 4-C₂H₅ |
| 4-OCH(C₂H₅)₂ | Cl | H | H | 4-Cl |
| 4-OC(CH₃)₂C₂H₅ | Cl | H | H | 4-Cl |
| 4-OC(CH₃)₂C₂H₅ | Cl | H | H | 4-C₂H₅ |
| 4-OCH(CH₃)C₄H₉ | Cl | H | H | 4-Cl |
| 4-OCH(CH₃)C₄H₉ | Cl | H | H | 4-C₂H₅ |
| 4-OCH₂CH(CH₃)C₃H₇ | Cl | H | H | 4-Cl |
| 4-OC₂H₄CH(CH₃)C₂H₅ | Cl | H | H | 4-Cl |
| 4-O(CH₂)₃CH(CH₃)₂ | Cl | H | H | 4-Cl |
| 4-OC₂H₄C(CH₃)₃ | Cl | H | H | 4-Cl |
| 4-OCH₂C(CH₃)₂C₂H₅ | Cl | H | H | 4-Cl |
| 4-OCH₂CH(C₂H₅)₂ | Cl | H | H | 4-Cl |
| 4-OCH(C₂H₅)C₃H₇ | Cl | H | H | 4-Cl |
| 4-OCH(CH₃)CH₂CH(CH₃)₂ | Cl | H | H | 4-Cl |
| 4-OCH(CH₃)CH₂CH(CH₃)₂ | Cl | H | H | 4-C₂H₅ |
| 4-OC₇H₁₅ | Cl | H | H | 4-Cl |
| 4-O(CH₂)₄CH(CH₃)CH₃ | Cl | H | H | 4-Cl |
| 4-O(CH₂)₄CH(CH₃)CH₃ | Cl | H | H | 4-C₂H₅ |
| 4-O(CH₂)₃CH(CH₃)C₂H₅ | Cl | H | H | 4-Cl |
| 4-O(CH₂)₃CH(CH₃)C₂H₅ | Cl | H | H | 4-C₂H₅ |
| 4-O(CH₂)₃CH(CH₃)C₃H₇ | Cl | H | H | 4-Cl |
| 4-O(CH₂)₃CH(CH₃)C₃H₇ | Cl | H | H | 4-C₂H₅ |
| 4-OCH₂CH(CH₃)C₄H₉ | Cl | H | H | 4-Cl |
| 4-OCH(CH₃)C₅H₁₁ | Cl | H | H | 4-Cl |

TABLE 1-continued

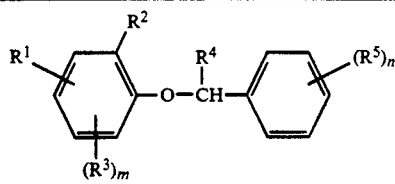

| $R^1$ | $R^2$ | $(R^3)_m$ | $R^4$ | $(R^5)_n$ |
|---|---|---|---|---|
| 4-OCH(CH$_3$)C$_5$H$_{11}$ | Cl | H | H | 4-C$_2$H$_5$ |
| 4-OC$_2$H$_4$CH(C$_2$H$_5$)$_2$ | Cl | H | H | 4-Cl |
| 4-OCH$_2$CH(C$_2$H$_5$)C$_3$H$_7$ | Cl | H | H | 4-Cl |
| 4-OCH(C$_2$H$_5$)C$_4$H$_9$ | Cl | H | H | 4-Cl |
| 4-OCH(C$_2$H$_5$)C$_4$H$_9$ | Cl | H | H | 4-C$_2$H$_5$ |
| 4-O(CH$_2$)$_3$C(CH$_3$)$_3$ | Cl | H | H | 4-Cl |
| 4-OCH$_2$C(CH$_3$)$_2$C$_3$H$_7$ | Cl | H | H | 4-Cl |
| 4-O(CH$_2$)$_5$CH(CH$_3$)$_2$ | Cl | H | H | 4-Cl |
| 4-O(CH$_2$)$_4$CH(CH$_3$)C$_2$H$_5$ | Cl | H | H | 4-Cl |
| 4-OCH(CH$_3$)C$_6$H$_{13}$ | Cl | H | H | 4-Cl |
| 4-OCH(CH$_3$)C$_6$H$_{13}$ | Cl | H | H | 4-C$_2$H$_5$ |
| 4-OC$_2$H$_4$CH(C$_2$H$_5$)C$_3$H$_7$ | Cl | H | H | 4-Cl |
| 4-O(CH$_2$)$_4$C(CH$_3$)$_2$ | Cl | H | H | 4-Cl |
| 4-O(CH$_2$)$_3$C(CH$_3$)$_2$C$_2$H$_5$ | Cl | H | H | 4-Cl |
| 4-OCH(C$_2$H$_5$)$_2$ | Cl | H | H | 4-Cl |
| 4-OC$_2$H$_4$C(C$_2$H$_5$)$_2$CH$_3$ | Cl | H | H | 4-Cl |
| 4-CH$_2$OC$_2$H$_5$ | Cl | H | H | 4-Cl |
| 4-C$_2$H$_4$OCH$_3$ | Cl | H | H | 4-Cl |
| 4-C$_2$H$_4$OCH$_3$ | Cl | H | H | 4-C$_2$H$_5$ |
| 4-CH(CH$_3$)OCH$_3$ | Cl | H | H | 4-Cl |
| 4-CH(CH$_3$)OCH$_3$ | Cl | H | H | 4-C$_2$H$_5$ |
| 4-C$_2$H$_4$OC$_2$H$_5$ | Cl | H | H | 4-Cl |
| 4-CH$_2$OC$_2$H$_5$ | Cl | H | H | 4-C$_2$H$_5$ |
| 4-(CH$_2$)$_3$OCH$_3$ | Cl | H | H | 4-Cl |
| 4-CH$_2$CH(CH$_3$)OCH$_3$ | Cl | H | H | 4-Cl |
| 4-CH$_2$CH(CH$_3$)OC$_2$H$_5$ | Cl | H | H | 4-Cl |
| 4-CH$_2$CH(OCH$_3$)C$_2$H$_5$ | Cl | H | H | 4-Cl |
| 4-CH$_2$CH(OC$_2$H$_5$)C$_2$H$_5$ | Cl | H | H | 4-Cl |
| 4-(CH$_2$)$_4$OCH$_3$ | Cl | H | H | 4-Cl |
| 4-CH(OCH$_3$)C$_2$H$_5$ | Cl | H | H | 4-Cl |
| 4-CH$_2$OC$_3$H$_7$ | Cl | H | H | 4-Cl |
| 4-CH$_2$OCH(CH$_3$)$_2$ | Cl | H | H | 4-Cl |
| 4-(CH$_2$)$_3$OC$_3$H$_7$ | Cl | H | H | 4-Cl |
| 4-(CH$_2$)$_4$OC$_3$H$_7$ | Cl | H | H | 4-Cl |
| 4-(CH$_2$)$_6$OC$_2$H$_5$ | Cl | H | H | 4-Cl |
| 4-(CH$_2$)$_6$OC$_2$H$_5$ | Cl | H | H | 4-C$_2$H$_5$ |
| 4-(CH$_2$)$_5$OC$_2$H$_5$ | Cl | H | H | 4-Cl |
| 4-(CH$_2$)$_4$OC$_2$H$_5$ | Cl | H | H | 4-Cl |
| 4-CH$_2$OCH(CH$_3$)C$_2$H$_5$ | Cl | H | H | 4-Cl |
| 4-CH$_2$OCH$_2$CH(CH$_3$)$_2$ | Cl | H | H | 4-Cl |
| 4-CH$_2$OCH(C$_2$H$_5$)$_2$ | Cl | H | H | 4-Cl |
| 4-CH$_2$OCH$_2$CH(C$_2$H$_5$)$_2$ | Cl | H | H | 4-Cl |
| 4-CH$_2$OCH$_2$CHC$_2$H$_5$<br>                                           C$_3$H$_7$ | Cl | H | H | 4-Cl |
| 4-CH$_2$OCH$_2$CH(C$_2$H$_5$)$_2$ | Cl | H | H | 4-Cl |
| 4-CH$_2$OC$_2$H$_4$CH(C$_2$H$_5$)$_2$ | Cl | H | H | 4-Cl |
| 4-CH$_2$CH=CH$_2$ | Cl | H | H | 4-Cl |
| 4-CH$_2$CH=CH$_2$ | Cl | H | H | 4-C$_2$H$_5$ |
| 4-CH=CHCH$_3$ | Cl | H | H | 4-Cl |
| 4-CH$_2$CH=CHCH$_3$ | Cl | H | H | 4-Cl |
| 4-CH$_2$C(CH$_3$)=CH$_2$ | Cl | H | H | 4-Cl |
| 4-CH$_2$CH=CHC$_2$H$_5$ | Cl | H | H | 4-Cl |
| 4-CH$_2$CH=C(CH$_3$)$_2$ | Cl | H | H | 4-Cl |
| 4-CH=CH-tert-C$_4$H$_9$ | Cl | H | H | 4-Cl |
| 4-CH$_2$C(CH$_3$)=CHCH$_3$ | Cl | H | H | 4-Cl |
| 4-CH=CHC$_3$H$_7$ | Cl | H | H | 4-Cl |
| 4-CH=CHC$_4$H$_9$ | Cl | H | H | 4-Cl |
| 4-CH$_2$CH=CHC$_3$H$_7$ | Cl | H | H | 4-Cl |
| 4-(CH$_2$)$_4$CH=CH$_2$ | Cl | H | H | 4-Cl |
| 4-CH$_2$CH(CH$_3$)CH=CH$_2$ | Cl | H | H | 4-Cl |
| 4-C(CH$_3$)$_2$CH=CH$_2$ | Cl | H | H | 4-Cl |
| 4-(CH$_2$)$_5$CH=CH$_2$ | Cl | H | H | 4-Cl |
| 4-(CH$_2$)$_6$CH=CH$_2$ | Cl | H | H | 4-Cl |
| 4-(CH$_2$)$_6$CH=CH$_2$ | Cl | H | H | 4-C$_2$H$_5$ |
| 4-OCH$_2$CH=CH$_2$ | Cl | H | H | 4-Cl |
| 4-OCH$_2$CH=CH$_2$ | Cl | H | H | 4-C$_2$H$_5$ |
| 4-OCH=CHCH$_3$ | Cl | H | H | 4-Cl |
| 4-OCH$_2$CH=CHCH$_3$ | Cl | H | H | 4-Cl |

TABLE 1-continued

| R¹ | R² | (R³)ₘ | R⁴ | (R⁵)ₙ |
|---|---|---|---|---|
| 4-OCH₂C(CH₃)=CH₂ | Cl | H | H | 4-Cl |
| 4-OCH₂CH=CHC₂H₅ | Cl | H | H | 4-Cl |
| 4-OCH₂CH=CHC₂H₅ | Cl | H | H | 4-C₂H₅ |
| 4-OCH₂CH=C(CH₃)₂ | Cl | H | H | 4-Cl |
| 4-OCH₂C(CH₃)=CHCH₃ | Cl | H | H | 4-Cl |
| 4-OCH₂CH=CHC₃H₇ | Cl | H | H | 4-Cl |
| 4-O(CH₂)₄CH=CH₂ | Cl | H | H | 4-Cl |
| 4-OCH₂CH(CH₃)CH=CH₂ | Cl | H | H | 4-Cl |
| 4-O(CH₂)₅CH=CH₂ | Cl | H | H | 4-Cl |
| 4-O(CH₂)₆CH=CH₂ | Cl | H | H | 4-Cl |
| 4-O(CH₂)₆CH=CH₂ | Cl | H | H | 4-C₂H₅ |
| 4-CH₂OCH₂CH=CH₂ | Cl | H | H | 4-Cl |
| 4-CH₂OCH₂CH=CH₂ | Cl | H | H | 4-C₂H₅ |
| 4-CH₂OCH=CH₂ | Cl | H | H | 4-Cl |
| 4-CH₂OCH₂CH=CHCH₂ | Cl | H | H | 4-Cl |
| 4-CH₂OC₂H₄CH=CH₂ | Cl | H | H | 4-Cl |
| 4-CH₂OCH₂C(CH₃)=CH₂ | Cl | H | H | 4-Cl |
| 4-CH₂OCH₂CH=CHC₂H₅ | Cl | H | H | 4-Cl |
| 4-CH₂OCH₂CH=CHC₂H₅ | Cl | H | H | 4-C₂H₅ |
| 4-CH₂OCH₂C=CH(CH₃)₂ | Cl | H | H | 4-Cl |
| 4-CH₂OCH₂C(CH₃)=CHCH₃ | Cl | H | H | 4-Cl |
| 4-CH₂OCH₂CH=CH(C₃H₇) | Cl | H | H | 4-Cl |
| 4-CH₂O(CH₂)₄CH=CH₂ | Cl | H | H | 4-Cl |
| 4-CH₂OCH₂CH(CH₃)CH=CH₂ | Cl | H | H | 4-Cl |
| 4-CH₂O(CH₂)₅CH=CH₂ | Cl | H | H | 4-Cl |
| 4-C₂H₄OCH₂CH=CH₂ | Cl | H | H | 4-Cl |
| 4-C₂H₄OCH₂CH=CH(CH₃) | Cl | H | H | 4-Cl |
| 4-C₂H₄OC₂H₄CHCH₂ | Cl | H | H | 4-Cl |
| 4-C₂H₄OCH₂C(CH₃)=CH₂ | Cl | H | H | 4-Cl |
| 4-C₂H₄OCH₂CH=CHC₂H₅ | Cl | H | H | 4-Cl |
| 4-C₂H₄OCH₂CH=C(CH₃)₂ | Cl | H | H | 4-Cl |
| 4-C₂H₄OCH₂C(CH₃)=CHCH₃ | Cl | H | H | 4-Cl |
| 4-C₂H₄OCH₂C(CH₃)=CHCH₃ | Cl | H | H | 4-C₂H₅ |
| 4-C₂H₄OCH₂CH=CHC₃H₇ | Cl | H | H | 4-Cl |
| 4-C₂H₄OCH₂CH=CHC₃H₇ | Cl | H | H | 4-C₂H₅ |
| 4-C₂H₄O(CH₂)₄CH=CH₂ | Cl | H | H | 4-Cl |
| 4-C₂H₄O(CH₂)₄CH=CH₂ | Cl | H | H | 4-C₂H₅ |
| 4-C₂H₄OCH₂CH(CH=CH₂)CH₃ | Cl | H | H | 4-Cl |
| 4-C₂H₄OCH₂CH(CH=CH₂)CH₃ | Cl | H | H | 4-C₂H₅ |

TABLE 1-continued

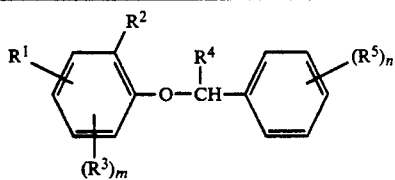

| R¹ | R² | (R³)_m | R⁴ | (R⁵)_n |
|---|---|---|---|---|
| 4-CHOCH$_2$CH=CH$_2$ <br> \|<br>CH$_3$ | Cl | H | H | 4-Cl |
| 4-CHOCH$_2$CH=CH$_2$ <br> \|<br>CH$_3$ | Cl | H | H | 4-C$_2$H$_5$ |
| 4-CHOCH$_2$CH=CHCH$_3$ <br> \|<br>CH$_3$ | Cl | H | H | 4-Cl |
| 4-CHOC$_2$H$_4$CH=CH$_2$ <br> \|<br>CH$_3$ | Cl | H | H | 4-Cl |
| 4-CHOCH$_2$C=CH$_2$ <br> \|  \|<br>CH$_3$  CH$_3$ | Cl | H | H | 4-Cl |
| 4-CHOCH$_2$CH=CH <br> \|  \|<br>CH$_3$  CH$_2$CH$_3$ | Cl | H | H | 4-Cl |
| 4-CHOCH$_2$CH=C(CH$_3$)$_2$ <br> \|<br>CH$_3$ | Cl | H | H | 4-Cl |
| 4-CHOCH$_2$C=CHCH$_3$ <br> \|  \|<br>CH$_3$  CH$_3$ | Cl | H | H. | 4-Cl |
| 4-CHOCH$_2$CH=CHC$_3$H$_7$ <br> \|<br>CH$_3$ | Cl | H | H | 4-Cl |
| 4-CHO(CH$_2$)$_4$CH=CH$_2$ <br> \|<br>CH$_3$ | Cl | H | H | 4-Cl |
| 4-CHO(CH$_2$)$_4$CH=CH$_2$ <br> \|<br>CH$_3$ | Cl | H | H | 4-C$_2$H$_5$ |
| 4-CHOCH$_2$CHCH=CH$_2$ <br> \|  \|<br>CH$_3$  CH$_3$ | Cl | H | H | 4-Cl |
| 4-(CH$_2$)$_3$Br | Cl | H | H | 4-Cl |
| 4-(CH$_2$)$_3$Br | Cl | H | H | 4-C$_2$H$_5$ |
| 4-(CH$_2$)$_3$Cl | Cl | H | H | 4-Cl |
| 4-(CH$_2$)$_3$Cl | Cl | H | H | 4-C$_2$H$_5$ |
| 4-(CH$_2$)$_4$Cl | Cl | H | H | 4-Cl |
| 4-(CH$_2$)$_5$Cl | Cl | H | H | 4-Cl |
| 4-(CH$_2$)$_5$Cl | Cl | H | H | 4-C$_2$H$_5$ |
| 4-(CH$_2$)$_6$Cl | Cl | H | H | 4-Cl |
| 4-(CH$_2$)$_7$Br | Cl | H | H | 4-Cl |
| 4-(CH$_2$)$_8$Br | Cl | H | H | 4-Cl |
| 4-(CH$_2$)$_8$Br | Cl | H | H | 4-C$_2$H$_5$ |
| 4-CH$_2$CH(Cl)CH$_3$ | Cl | H | H | 4-Cl |
| 4-CH(CH$_3$)CH(Cl)CH$_3$ | Cl | H | H | 4-Cl |
| 4-C$_2$H$_4$CH(Cl)CH$_3$ | Cl | H | H | 4-Cl |
| 4-CH$_2$CH(Cl)CH$_3$ | Cl | H | H | 4-C$_2$H$_5$ |
| 4-CH$_2$CH(Cl)CH$_2$Cl | Cl | H | H | 4-Cl |
| 4-CH$_2$CF$_2$CF$_3$ | Cl | H | H | 4-Cl |
| 4-CH$_2$CF$_2$CF$_3$ | Cl | H | H | 4-C$_2$H$_5$ |
| 4-CH(CH$_3$)CF$_2$CF$_3$ | Cl | H | H | 4-Cl |

TABLE 1-continued

[Structure: R¹ and R² on one benzene ring with (R³)ₘ, connected via O—CH(R⁴) to another benzene ring with (R⁵)ₙ]

| R¹ | R² | (R³)ₘ | R⁴ | (R⁵)ₙ |
|---|---|---|---|---|
| 4-(CH₂)₃F | Cl | H | H | 4-Cl |
| 4-(CH₂)₃F | Cl | H | H | 4-C₂H₅ |
| 4-(CH₂)₄F | Cl | H | H | 4-Cl |
| 4-(CH₂)₅F | Cl | H | H | 4-Cl |
| 4-O(CH₂)₃Br | Cl | H | H | 4-Cl |
| 4-O(CH₂)₃Cl | Cl | H | H | 4-Cl |
| 4-O(CH₂)₄Cl | Cl | H | H | 4-Cl |
| 4-O(CH₂)₄Br | Cl | H | H | 4-Cl |
| 4-O(CH₂)₅Cl | Cl | H | H | 4-Cl |
| 4-O(CH₂)₅Cl | Cl | H | H | 4-C₂H₅ |
| 4-O(CH₂)₆Cl | Cl | H | H | 4-Cl |
| 4-O(CH₂)₇Br | Cl | H | H | 4-Cl |
| 4-O(CH₂)₈Br | Cl | H | H | 4-Cl |
| 4-O(CH₂)₈Br | Cl | H | H | 4-C₂H₅ |
| 4-OCH₂CH(Cl)CH₃ | Cl | H | H | 4-Cl |
| 4-OCH₂CH(Cl)CH₃ | Cl | H | H | 4-C₂H₅ |
| 4-OCH(CH₃)CH(Cl)CH₃ | Cl | H | H | 4-Cl |
| 4-OCH₂CH(Br)CH₃ | Cl | H | H | 4-Cl |
| 4-OC₂H₄CH(Cl)CH₃ | Cl | H | H | 4-Cl |
| 4-OC₂H₄CH(Br)CH₃ | Cl | H | H | 4-Cl |
| 4-OCH₂CH(Cl)CH₂Cl | Cl | H | H | 4-Cl |
| 4-OCH₂(CHCl)₂CH₂Cl | Cl | H | H | 4-Cl |
| 4-OCH₂CF₂CF₃ | Cl | H | H | 4-Cl |
| 4-OCH₂CF₂CF₃ | Cl | H | H | 4-C₂H₅ |
| 4-OCH(CH₃)CF₂CF₃ | Cl | H | H | 4-Cl |
| 4-OC₂H₄CH₂F | Cl | H | H | 4-Cl |
| 4-O(CH₂)₃CH₂F | Cl | H | H | 4-Cl |
| 4-O(CH₂)₄CH₂F | Cl | H | H | 4-Cl |
| 4-CH₂OC₂H₄Br | Cl | H | H | 4-Cl |
| 4-CH₂OC₂H₄Br | Cl | H | H | 4-C₂H₅ |
| 4-CH₂O(CH₂)₃Cl | Cl | H | H | 4-Cl |
| 4-CH₂O(CH₂)₃Cl | Cl | H | H | 4-C₂H₅ |
| 4-CH₂O(CH₂)₄Cl | Cl | H | H | 4-Cl |
| 4-CH₂O(CH₂)₅Cl | Cl | H | H | 4-Cl |
| 4-CH₂O(CH₂)₅Cl | Cl | H | H | 4-C₂H₅ |
| 4-CH₂O(CH₂)₆Cl | Cl | H | H | 4-Cl |
| 4-CH₂O(CH₂)₇Br | Cl | H | H | 4-Cl |
| 4-CH₂O(CH₂)₇Br | Cl | H | H | 4-C₂H₅ |
| 4-CH₂OCH₂CHClCH₃ | Cl | H | H | 4-Cl |
| 4-CH₂OCH(CH₃)CH(Cl)CH₃ | Cl | H | H | 4-Cl |
| 4-CH₂OCH₂CHBrCH₃ | Cl | H | H | 4-Cl |
| 4-CH₂OC₂H₄CHClCH₃ | Cl | H | H | 4-Cl |
| 4-CH₂OC₂H₄CHBrCH₃ | Cl | H | H | 4-Cl |
| 4-CH₂OCHCH(Cl)CH₂Cl | Cl | H | H | 4-Cl |
| 4-CH₂OCH(CH₃)C₂F₅ | Cl | H | H | 4-Cl |
| 4-CH₂O(CH₂)₃F | Cl | H | H | 4-Cl |
| 4-CH₂O(CH₂)₃F | Cl | H | H | 4-C₂H₅ |
| 4-CH₂O(CH₂)₄F | Cl | H | H | 4-Cl |
| 4-CH₂O(CH₂)₅F | Cl | H | H | 4-Cl |
| 4-CH₂O(CH₂)₆F | Cl | H | H | 4-Cl |
| 4-CH₂O(CH₂)₇F | Cl | H | H | 4-Cl |
| 4-CH₂O(CH₂)₇F | Cl | H | H | 4-C₂H₅ |
| 4-CH(CH₃)O(CH₂)₃Br | Cl | H | H | 4-Cl |
| 4-CH(CH₃)O(CH₂)₃Br | Cl | H | H | 4-C₂H₅ |
| 4-CH(CH₃)O(CH₂)₃Cl | Cl | H | H | 4-Cl |
| 4-CH(CH₃)O(CH₂)₄Cl | Cl | H | H | 4-Cl |
| 4-CH(CH₃)O(CH₂)₄Br | Cl | H | H | 4-Cl |
| 4-CH(CH₃)O(CH₂)₅Cl | Cl | H | H | 4-Cl |
| 4-CH(CH₃)O(CH₂)₆Cl | Cl | H | H | 4-Cl |
| 4-CH(CH₃)O(CH₂)₆Br | Cl | H | H | 4-Cl |
| 4-CH(CH₃)OCH₂CH(Cl)CH₃ | Cl | H | H | 4-Cl |

TABLE 1-continued

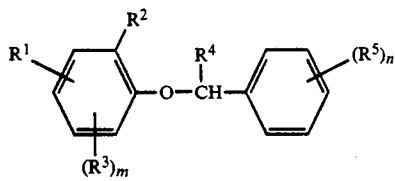

| R¹ | R² | (R³)ₘ | R⁴ | (R⁵)ₙ |
|---|---|---|---|---|
| 4-CH(CH₃)—O—CH(CH₃)—CHClCH₃ | Cl | H | H | 4-Cl |
| 4-CH(CH₃)OCH₂CH(Br)CH₃ | Cl | H | H | 4-Cl |
| 4-CH(CH₃)OC₂H₄CH(Cl)CH₃ | Cl | H | H | 4-Cl |
| 4-CH(CH₃)OC₂H₄CH(Cl)CH₃ | Cl | H | H | 4-C₂H₅ |
| 4-CH(CH₃)OC₂H₄CH(Br)CH₃ | Cl | H | H | 4-Cl |
| 4-CH(CH₃)OCH₂CHClCH₂Cl | Cl | H | H | 4-Cl |
| 4-CH(CH₃)OCH₂CHClCH₂Cl | Cl | H | H | 4-C₂H₅ |
| 4-CH(CH₃)OCH(CH₃)C₂F₅ | Cl | H | H | 4-Cl |
| 4-CH(CH₃)OCH(CH₃)C₂F₅ | Cl | H | H | 4-C₂H₅ |
| 4-CH(CH₃)O(CH₂)₃F | Cl | H | H | 4-Cl |
| 4-CH(CH₃)O(CH₂)₃F | Cl | H | H | 4-C₂H₅ |
| 4-CH(CH₃)O(CH₂)₄F | Cl | H | H | 4-Cl |
| 4-CH(CH₃)O(CH₂)₅F | Cl | H | H | 4-Cl |
| 4-CH(CH₃)O(CH₂)₆F | Cl | H | H | 4-Cl |
| 4-C₂H₄O(CH₂)₃Br | Cl | H | H | 4-Cl |
| 4-C₂H₄O(CH₂)₃Br | Cl | H | H | 4-C₂H₅ |
| 4-C₂H₄O(CH₂)₃Cl | Cl | H | H | 4-Cl |
| 4-C₂H₄O(CH₂)₃I | Cl | H | H | 4-Cl |
| 4-C₂H₄O(CH₂)₄Cl | Cl | H | H | 4-Cl |
| 4-C₂H₄O(CH₂)₄Br | Cl | H | H | 4-Cl |
| 4-C₂H₄O(CH₂)₄Cl | Cl | H | H | 4-C₂H₅ |
| 4-C₂H₄O(CH₂)₅Cl | Cl | H | H | 4-Cl |
| 4-C₂H₄O(CH₂)₅Br | Cl | H | H | 4-Cl |
| 4-C₂H₄O(CH₂)₆Cl | Cl | H | H | 4-Cl |
| 4-C₂H₄O(CH₂)₆Br | Cl | H | H | 4-Cl |
| 4-C₂H₄O(CH₂)₆Br | Cl | H | H | 4-C₂H₅ |
| 4-C₂H₄OCH₂CH(Cl)CH₃ | Cl | H | H | 4-Cl |
| 4-C₂H₄OCH(CH₃)—CH(Cl)CH₃ | Cl | H | H | 4-Cl |
| 4-C₂H₄OCH₂CHBrCH₃ | Cl | H | H | 4-Cl |
| 4-C₂H₄OC₂H₄CH(Cl)CH₃ | Cl | H | H | 4-Cl |
| 4-C₂H₄OC₂H₄CH(Br)CH₃ | Cl | H | H | 4-Cl |
| 4-C₂H₄OCH₂CH(Cl)CH₂Cl | Cl | H | H | 4-Cl |

TABLE 1-continued $$\underset{(R^3)_m}{\overset{R^2}{\underset{}{\bigcirc}}}\text{O}-\overset{R^4}{\underset{}{CH}}\underset{}{\bigcirc}(R^5)_n$$

| R$^1$ | R$^2$ | (R$^3$)$_m$ | R$^4$ | (R$^5$)$_n$ |
|---|---|---|---|---|
| 4-C$_2$H$_4$OCH(C$_2$F$_5$)CH$_3$ | Cl | H | H | 4-Cl |
| 4-C$_2$H$_4$O(CH$_2$)$_3$F | Cl | H | H | 4-Cl |
| 4-C$_2$H$_4$O(CH$_2$)$_3$F | Cl | H | H | 4-C$_2$H$_5$ |
| 4-C$_2$H$_4$O(CH$_2$)$_4$F | Cl | H | H | 4-Cl |
| 4-C$_2$H$_4$O(CH$_2$)$_5$F | Cl | H | H | 4-Cl |
| 4-C$_2$H$_4$O(CH$_2$)$_6$F | Cl | H | H | 4-Cl |
| 4-C$_2$H$_4$O(CH$_2$)$_6$F | Cl | H | H | 4-C$_2$H$_5$ |
| 4-CH$_2$C(Cl)=CH$_2$ | Cl | H | H | 4-Cl |
| 4-CH$_2$C(Cl)=CH$_2$ | Cl | H | H | 4-C$_2$H$_5$ |
| 4-CH$_2$C(Br)=CH$_2$ | Cl | H | H | 4-Cl |
| 4-CH$_2$CH=C(Cl)CH$_3$ | Cl | H | H | 4-Cl |
| 4-CH$_2$CH=C(Cl)CH$_3$ | Cl | H | H | 4-C$_2$H$_5$ |
| 4-(CH$_2$)$_6$C(Cl)=CH$_2$ | Cl | H | H | 4-Cl |
| 4-CH$_2$CH=CHCl | Cl | H | H | 4-Cl |
| 4-OCH$_2$C(Cl)=CHCl | Cl | H | H | 4-Cl |
| 4-OCH$_2$C(Cl)=CHCl | Cl | H | H | 4-C$_2$H$_5$ |
| 4-OCH$_2$C(Cl)=CH$_2$ | Cl | H | H | 4-Cl |
| 4-OCH$_2$C(Br)=CH$_2$ | Cl | H | H | 4-Cl |
| 4-OCH$_2$CH(Cl)CH=CH$_2$ | Cl | H | H | 4-Cl |
| 4-OCH$_2$CH=C(Cl)CH$_3$ | Cl | H | H | 4-Cl |
| 4-OCH$_2$CH=CHCl | Cl | H | H | 4-Cl |
| 4-O(CH$_2$)$_6$C(Cl)=CH$_2$ | Cl | H | H | 4-Cl |
| 4-OCH$_2$C(Cl)=CHCl | Cl | H | H | 4-Cl |
| 4-CH$_2$OCH$_2$CCl=CH$_2$ | Cl | H | H | 4-Cl |
| 4-CH$_2$OCH$_2$CBr=CH$_2$ | Cl | H | H | 4-Cl |
| 4-CH$_2$OCH$_2$CH=C(Cl)CH$_3$ | Cl | H | H | 4-Cl |
| 4-CH$_2$OCH$_2$CH=C(Cl)CH$_3$ | Cl | H | H | 4-C$_2$H$_5$ |
| 4-CH$_2$O(CH$_2$)$_5$C(Cl)=CH$_2$ | Cl | H | H | 4-Cl |
| 4-CH$_2$OCH$_2$CH=CHCl | Cl | H | H | 4-Cl |
| 4-CH$_2$OCH=C(Cl)-CHCl(Cl) | Cl | H | H | 4-Cl |
| 4-CH$_2$OCH$_2$C(Cl)=CHCl | Cl | H | H | 4-Cl |
| 4-CH(CH$_3$)OCH$_2$C(Cl)=CH$_2$ | Cl | H | H | 4-Cl |
| 4-CH(CH$_3$)OCH$_2$C(Cl)=CH$_2$ | Cl | H | H | 4-C$_2$H$_5$ |
| 4-CH(CH$_3$)OCH$_2$C(Br)=CH$_2$ | Cl | H | H | 4-Cl |
| 4-CH(CH$_3$)OCH$_2$CH=CHCl | Cl | H | H | 4-Cl |
| 4-CH(CH$_3$)OCH$_2$CH=CHCl | Cl | H | H | 4-C$_2$H$_5$ |

TABLE 1-continued

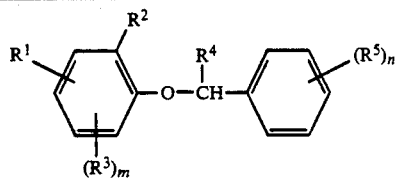

| R¹ | R² | (R³)ₘ | R⁴ | (R⁵)ₙ |
|---|---|---|---|---|
| 4-CHOCH₂C=CHCl (with CH₃ and Cl substituents) | Cl | H | H | 4-Cl |
| 4-C₂H₄OCH₂C=CH₂ (Cl) | Cl | H | H | 4-Cl |
| 4-C₂H₄OCH₂C=CH₂ (Cl) | Cl | H | H | 4-C₂H₅ |
| 4-C₂H₄OCH₂C=CH₂ (Br) | Cl | H | H | 4-Cl |
| 4-C₂H₄OCH₂CH=CCH₃ (Cl) | Cl | H | H | 4-Cl |
| 4-C₂H₄OCH₂CH=CHCl | Cl | H | H | 4-Cl |
| 4-C₂H₄OCH₂CH=CHCl | Cl | H | H | 4-C₂H₅ |
| 4-C₂H₄OCH₂C=CHCl (Cl) | Cl | H | H | 4-Cl |
| 4-OCH₂C≡CH | Cl | H | H | 4-Cl |
| 4-OCH₂C≡CH | Cl | H | H | 4-C₂H₅ |
| 4-OCH₂C≡CCH₃ | Cl | H | H | 4-Cl |
| 4-OCH₂C≡CC₂H₅ | Cl | H | H | 4-Cl |
| 4-OCH₂C≡CC₂H₅ | Cl | H | H | 4-C₂H₅ |
| 4-OCH₂C≡CC₃H₇ | Cl | H | H | 4-Cl |
| 4-OCH₂C≡CC₄H₉ | Cl | H | H | 4-Cl |
| 4-OCH₂C≡CC₅H₁₁ | Cl | H | H | 4-Cl |
| 4-OCH₂C≡CC₅H₁₁ | Cl | H | H | 4-C₂H₅ |
| 4-OCH(CH₃)C≡CH | Cl | H | H | 4-Cl |
| 4-OCH(C₂H₅)C≡CH | Cl | H | H | 4-Cl |
| 4-OCH(C₂H₅)C≡CH | Cl | H | H | 4-C₂H₅ |
| 4-OCH(C₃H₇)C≡CH | Cl | H | H | 4-Cl |
| 4-OCH(C₂H₅)C≡CCH₃ | Cl | H | H | 4-Cl |
| 4-OCH(C₃H₇)C≡CCH₃ | Cl | H | H | 4-Cl |
| 4-OCH₂C≡C-iso-C₃H₇ | Cl | H | H | 4-Cl |
| 4-OCH(CH₃)C≡C (iso-C₃H₇) | Cl | H | H | 4-Cl |
| 4-OCHC≡CCH(CH₃)₂ (C₂H₅) | Cl | H | H | 4-Cl |
| 4-OC₂H₄C≡CC₂H₅ | Cl | H | H | 4-Cl |
| 4-OCH(C₃H₇)C≡CCH₃ | Cl | H | H | 4-Cl |
| 4-OCH(C₃H₇)C≡CCH₃ | Cl | H | H | 4-C₂H₅ |
| 5-O-sec-C₄H₉ | Cl | H | H | 4-Cl |
| 5-O-sec-C₄H₉ | Cl | H | H | 4-C₂H₅ |
| 5-O-sec-C₄H₉ | Cl | 4-Cl | H | 4-Cl |
| 5-O-sec-C₄H₉ | Cl | 4-Cl | H | 4-C₂H₅ |
| 5-O-sec-C₄H₉ | Cl | 4-F | H | 4-Cl |
| 5-O-sec-C₄H₉ | Cl | 4-F | H | 4-C₂H₅ |

Examples of the insect pests against which the aromatic compounds (I) of the invention exhibit controlling effects are as shown below.

Hemiptera

Planthoppers such as brown planthopper (*Nilaparvata lugens*), white-backed rice planthopper (*Sogatella furcifera*) and small brown planthopper (*Laodelphax striatellus*); leafhoppers such as green rice leafhopper (*Nephotettix cincticeps*), *Nephotettix virescense*, *Nephotettix nigropictus*, zig-zag rice leafhopper (*Recilia dorsalis*), tea green leafhopper (*Empoasca onukii*) and grape leafhopper (*Arboridia apicalis*); aphids such as cotton aphid (*Aphis gossypii*) and green peach aphid (*Myzus persicae*); bugs; whiteflies (Aleyrodiidae) such as sweet potato whitefly (*Bemisia tabaci*) and greenhouse whitefly (*Trialeurodes vaporariorum*); scales; mealy bugs; lace bugs (Tingidae); psyllids (Psyllidae), etc.

Lepidoptera

Pyralid moths (Pyralidae) such as rice stem borer (*Chilo suppressalis*), rice leafroller (*Cnaphalocrocis medinalis*) and Indian meal moth (*Plodia interpunctella*); Noctuidae such as tobacco curworm (*Spodoptera litura*), rice armyworm (*Pseudaletia separate*), cabbage armyworm (*Mamestra brassicae*) and beet semi-looper (*Autographa nigrisigna*); Agrothis spp. such as turnip cutworm (*Agrothis segetum*) and black cutworm (*Agrothis ipsilon*); Heliothis spp.; Pieridae such as common cabbageworm (*Pieris rapae crucivora*); tortricid moths (Tortricidae) such as Adoxophyes spp. and Grapholita spp.; Carposinidae such as lyonetiid moths (Lyonetiidae), leaf-blotch miners (Gracillariidae), gelechiid moths (Gelechiidae) and tussock moths (Lymantriidae); diamondback moth (*Plutella xylostella*), clothes moths (Tineidae), casemaking clothes moth (*Tinea translucens*) and webbing clothes moth (*Tineola bisselliella*), etc.

Diptera

Mosquitos (Calicidae) such as common mosquito (*Culex pipiens pallens*) and *Culex tritaeniorhynchus*; Aedes spp. such as *Aedes aegypti* and *Aedes albopictus*; Anopheles spp. such as *Anopheles sinensis*; midges (Chironomidae); Muscidae such as housefly (*musca domestica*) and false stablefly (*Muscina stabulans*); Calliphoridae; Sarcophagidae; lesser housefly (*Fannia canicularis*); anthomyiid flies (Anthomyiidae) such as seedcorn maggot (*Delia platura*) and onion maggot (*Delia antique*); fruit flies (Tephritidae); shore flies (Ephydridae); small fruit flies (Drosophilidae); moth flies (Psychodidae); black flies (Simuliidae); Tabanidae; stable flies (Stomoxyidae); etc.

Coleoptera

Leaf beetles (Chrysomelidae) such as cucurbit beetle (*Aulacophora femoralis*), striped flea beetles (*Phyllotrata striolata*), western corn rootworm (*Diabrotica virgifora*) and southern corn root worm (*Diabrotica undecimpunctata*); scarabs (Scarabaeidae) such as cupreous chafer (*Anomala cuprea*) and soybeen beetle (*Anomala rufocuprea*); weevils (Cureulionidae) such as maize weevil (*Sitophilus zeamais*), rice water weevil (*Lissorhoptrus oryzophilus*) and adzuki bean weevil (*Callosobruchys chineneis*), etc.; darkling beetles (Tenebrionidae) such as yellow mealworm (*Tenebrio moliter*) and red flour beetles (*Tribolium castaneum*); Anobiidae; Coccinellidae such as twenty-eight-spotted ladybirds (*Epilachna vigintioctopunctata*); powderpost beetles (Lyctidae); false powderpost beetles (Bostrychidae); Cerambysidae, etc.

Dictyoptera

Blattellidae such as German cockroach (*Blattella germanica*); Blattidae such as smokybrown cockroach (*Periplaneta fuliginosa*), American cockroach (*Periplaneta americana*), brown cockroach (*Periplaneta brunnea*) and oriental cockroach (*Blatta orientalis*), etc.

Thysanoptera

Thrips such as *Thrips palmi*, yellow tea thrips (*Scirtothrips dorsalis*) and flower thrips (*Thrips hawaiiensis*), etc.

Hymenoptera

Ants (Formicidae); sawflies (Tenthredinidae) such as cabbage sawfly (*Athalia rosae ruficornis*), etc.

Orthoptera

Mole crickets (Gryllotalpidae); grasshoppers Acrididae), etc.

Aphaniptera

*Purex irritans*, etc.

Anoplura

*Pediculus humanus capitis*, *Phthirus pubis*, etc.

Isoptera

*Reticulitermes speratus*, Formosan subterrauean termite (*Coptotermes formosanus*), etc.

Among the insect pests as above exemplified, the aromatic compounds (I) are particularly effective in controlling those belonging to Hemiptera and also exhibit a remarkable controlling effect on planthoppers and leaf-hoppers in a field of rice plant or aphids.

The aromatic compounds (I) may be used alone as insecticides or in mixtures with other insecticides and-/or acaricides to enhance or expand their insecticidal or pesticidal use.

Examples of the other insecticides and/or acaricide include organophosphorus compounds (e.g. fenitrothion (O,O-dimethyl O-(3-methyl-4-nitrophenyl)phosphorothioate), fenthion (O,O-dimethyl O-[3-methyl-4-(methylthio)phenyl]-phosphorothioate), diazinon (O,O-diethyl-O-(2-isopropyl-6-methyl-pyrimidin-4-yl)phosphorothioate), chlorpyrifos (O,O-diethyl-O-(3,5,6-trichloro-2-pyridyl)phosphorothioate), acephate (O,S-dimethyl acetylphosphoramidothioate), methidathion (S-2,3-dihydro-5-methoxy-2-oxo-1,3,4-thiadiazol-3-ylmethyl O,O-dimethylphosphorodithioate), disulfoton (O,O-diethyl S-2-ethylthioethyl phosphorothioate), DDVP (2,2-dichlorovinyldimethylphosphate), sulprofos (O-ethyl O-4-(methylthio)phenyl S-propyl phosphorodithioate), cyanophos (O-4-cyanophenyl O,O-dimethyl phosphorothioate), dioxabenzofos (2-methoxy-4H-1,3,2-benzodioxaphosphinine-2-sulphide), dimethoate (O,O-diethyl-S-(N-methylcarbamoylmethyl)dithiophosphate), phenthoate (ethyl 2-dimethoxyphosphinothioylthio(phenyl)acetate), malathion (diethyl (dimethoxyphosphinothioylthio)succinate), trichlorfon (dimethyl 2,2,2-trichloro-1-hydroxyethylphosphonate), azinphos-methyl (S-3,4-dihydro-4-oxo-1,2,3-benzotriazin-3-ylmethyl O,O-dimethylphosphorodithioate) and monocrotophos (dimethyl (E)-1-methyl-2-(methylcarbamoyl)vinyl phosphate), etc.); carbamate derivatives (e.g. BPMC (2-sec-butylphenyl methylcarbamate), benfuracarb (ethyl N-[2,3-dihydro-2,2-dimethylbenzofuran-7-yloxycarbonyl(methyl)aminothio]-N-isopropyl-beta-alaninate), propoxur (2-isopropoxyphenyl N-methylcarbamate), carbosulfan (2,3-dihydro-2,2-dimethyl-7-benzo[b]furanyl N-methylcarbamate), carbaryl (1-naphthyl-N-methylcarbamate), methomyl (S-methyl-N-[(methylcarbamoyl)oxy]thioacetimidate), ethiofencarb (2-(ethylthiomethyl)phenyl methylcarbamate), aldicarb (2-methyl-2-(methylthio)propionaldehyde O-methylcarbamoyloxime) and Oxamyl (N,N-dimethyl-2-methylcarbamoyloxyimino-2-(methylthio)acetamide), etc.); pyrethroides (e.g. ethofenprop (2-(4-ethoxyphenyl-2-methylpropyl-3-phenoxybenzylether), fenvalerate ((RS)-alpha-cyano-3-phenoxybenzyl (RS)-2-(4-chlorophenyl)-3-methylbutyrate), esfenvalerate ((S)-alpha-cyano-3-phenoxybenzyl (S)-2-(4-chlorophenyl)-3-methylbutyrate), fenpropathrin ((RS)-alpha-cyano-3-phenoxybenzyl 2,2,3,3-tetramethylcyclopropanecarboxylate), cypermethrin ((RS)-alpha-cyano-3-phenoxybenzyl (1RS,3RS)-(1RS,3RS)-3-(2,2-dichlorovinyl)-2,2-dimethylcyclopropanecarboxylate), permethrin (3-phenoxybenzyl (1RS,3RS)-(1RS,3RS)-3-(2,2-dichlorovinyl)-2,2-dimethylcyclopropanecarboxylate), cyhalothrin ((R,S)-alpha-cyano-3-phenoxybenzyl (Z)-(1RS,3RS)-3-(2-chloro-3,3,3-trifluoropropenyl)-2,2-dimethylcyclopropanecarboxylate), deltamethrin ((S)-alpha-cyano-m-phenoxybenzyl (1R,3R)-3-(2,2-dibromovinyl)-2-dimethylcyclopropanecarboxylate) and cycloprothrin ((RS)-alpha-cyano-3-phenoxybenzyl (RS)-2,2-dichloro-1-(4-ethoxyphenyl)cyclopropanecarboxylate), etc.); thiadiazine derivatives (e.g. buprofezin (2-tert-butylimino-3-isopropyl-5-phenyl-1,3,5-triadiazin-4-one), etc.); nitroimidazolidine derivatives (e.g. imidacloprid (1-(6-chloro-3-pyridylmethyl)-N-nitroimidazolidin-2-ylideneamine), etc.); nereistoxin derivatives (e.g. cartap (S,S'-(2-dimethylaminotrimethylene) bis(thiocarbamate), thiocyclam (N,N-dimethyl-1,2,3-trithian-5-ylamine) and bensultap (S,S'-2-dimethylaminotrimethylene di(benzenethiosulphonate), etc.); halogenated hydrocarbons (e.g. endosulfan (6,7,8,9,10,10-hexachloro-1,5,5a,6,9,9a-hexahydro-6,9-methano-2,4,3-benzodioxathiepin-3-oxide) and gamma-BHC (1,2,3,4,5,6-hexachlorocyclohexane), etc.); benzoylphenylurea derivatives (e.g. chlorfluazuron (1-[3,5-dichloro-4-(3-chloro-5-trifluoromethylpyridin-2-yloxy)phehyl]-3-(2,6-difluorobenzoyl)urea), teflubenzuron (1-(3,5-dichloro-2,4-difluorophenyl)-3-(2,6-difluorobenzoyl)urea, and flufenoxuron (1-[4-(2-chloro-4-trifluoromethylphenoxy)-2-fluorophenyl]-3-(2,6-difluorobenzoyl)urea, etc.); formamidine derivatives (e.g. amitraz (N,N'-[(methylimino)dimethylidyne]-di-2,4-xylidine) and chlordimeform (N'-(4-chloro-2-methylphenyl)-N,N-dimethylmethanimidamide), etc.).

On the practical use of the aromatic compounds (I) as insecticides, they may be employed as such but are normally mixed with appropriate additives such as solid carriers, liquid carriers, gaseous carriers, feed, etc. to formulate their compositions. When desired or necessary, surfactants and other adjuvants may be further incorporated therein. The compositions may be prepared into any conventional forms such as oil sprays, emulsifiable concentrates, wettable powders, flowable concentrates (e.g. water-based suspension formulations, water-based emulsion formulations), granules, dusts, aerosals, heating smoking formulations (e.g. self-burning-type smoking formulations, chemical reaction-type smoking formulations, porous ceramic plate-type smoking formulations), ULV formulations, poison baits, etc.

The composition of the invention contains generally the aromatic compound(s) (I) as the active ingredient in an amount of from about 0.001% to 95% by weight based on the composition.

Examples of the solid carrier usable for making the composition are fine powders or granules of clays (e.g. kaolin clay, diatomaceous earth, synthetic hydrated silica, bentonite, Fubasami clay, terra alba), talc, ceramics, other inorganic minerals (e.g. sericite, quartz, sulfur, activated carbon, calcium carbonate, hydrated silica), chemical fertilizers (e.g. ammonium sulfate, ammonium phosphate, ammonium nitrate, urea, ammonium chloride), etc. Examples of the liquid carrier include water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitriles, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethylsulfoxide, vegetable oils (e.g. soybean oil, cotton seed oil), etc. Examples of the gaseous carrier, i.e. a propellant, include freon gas, butane gas, LPG (liquefied petroleum gas), dimethyl ether, carbon dioxide, etc.

Examples of the surfactant are alkylsulfates, alkylsulfonates, alkylarylsulfonates, alkyl aryl ethers and polyoxyethylene derivatives thereof, polyethylene glycol ethers, polyvalent alcohol esters, sugar alcohol derivatives, etc. Examples of the adjuvants such as binders and dispersing agents are casein, gelatin, polysaccharides (e.g. starch powders, gum arabic, cellulose derivatives, alginic acid), lignin derivatives, bentonite, sugars, synthetic water-soluble high molecular weight substances (e.g. polyacrylic alcohol, polyvinylpyrrolidone, polyacrylic acid), etc. Examples of the stabilizer include PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids or esters thereof, etc.

The base material for self-burning-type smoking formulations may include, for example, burning heat-generating agents such as nitrates, nitrites, guanidine salts, potassium chlorate, nitrocellulose, ethyl cellulose and wood powders, pyrolysis-promoting agents such as alkali metal salts, alkaline earth metal salts, dichromates and chromates, oxygen-supplying agents such as potassium nitrate, burning-supporting agents such as melamine and wheat starch, extenders such as diatomaceous earth, binders such as synthetic pastes, etc. The base material for chemical reation-type smoking formulations can include, for example, heat-generating agents such as alkali metal sulfides, alkali metal polysulfides, alkali metal hydrosulfides, hydrated salts of alkali metals and calcium oxide, catalyzing agents such as carbonaceous substances, iron carbide and activated clay, organic foaming agents such as azodicarbonamide, benzenesulfonyl hydrazides, dinitrosopentamethylenetetramine, polystyrene and polyurethane, fillers such as natural fiber pieces and synthetic fiber pieces, etc. The base material for poison baits may contain feed components such as crop powders, essential vegetable oil, sugars and crystalline cellulose, antioxidants such as dibutylhydroxyrtolune and nordihydroguaiaretic acid, preservatives such as dehydroacetic acid, feeding error preventing agnets such as red paper powders, incentive flavors such as cheese flavor and onion flavor, etc.

Flowable concentrates (water-based suspension or emulsion formulations) are generally obtained by dispersing about 1 to 75 parts by weight of the aromatic compound (I) as the active ingredient finely and uniformly into water containing about 0.5 to 15 parts by weight of a dipersing agent, about 0.1 to 10 parts by weight of a suspending agent (e.g. protective colloids, compounds giving a thixotropic property) and optionally about 0 to 10 parts by weight of an auxiliary agent(s) such as a defoaming agent, an anticorrosive agent, a stabilizing agent, a spreading agents, penetration auxiliaries, antifreezing agent, an antibacterial agent, an antimolding agent and the like. The use of an oil, into which the active ingredient is hardly soluble, in place of water affords oil-based suspension formulations. Examples of the protective colloids as above mentioned are gelatin, casein, gums, cellulose ethers, polyvinyl alcohol, etc. Examples of the compounds giving a thixotropic property are bentonite, aluminum magnesium silicate, xanthane gum, polyacrylic acid, etc.

The composition of the invention thus obtained may be used as such or after diluting with water. It may be also used in a mixture with any other active component or composition chosen from insecticides, nematocides, acaricides, fungicides, bacteriocides, herbicides, plant growth regulators, synergistic agents, fertilizers, soil conditioners, animal feed, etc. Alternatively, the composition of the invention may be applied separately but simultaneously with said other active component or composition.

For the purpose of controlling insect pests in the agricultural field, the aromatic compound (I) according to the present invention may be applied to the insect pests or the locus where the insect pests propagate generally in an amount of about 0.001 g to 500 g, and preferably about 0.1 g to 500 g per 10 ares. when the aromatic compound (I) is applied in a form of emulsifiable concentrate, wettable powder, flowable concentrate or the like after dilution with water, its concentration may be from about 0.0001 to 1000 ppm. Granules, dusts, etc. may be used as such, i.e. without water dilution. When the aromatic compound (I) is used for household or public hygiene, it may be used in the form of emulsifiable concentrate, wettable powder, flowable concentrate or the like with water dilution, etc. In this case, the concentration of the active ingredient may be from about 0.0001 to 10,000 ppm. In case of oils, aerosol, fumigants, ULV formulations, poison baits, etc., they may be applied as such. However, the doses and concentrations may vary within broad ranges depending upon the composition, the application time, the place applied, the application method, the kind of insect pests, the condition of damage, etc. and may be increased or decreased, irrespective of the general ranges set forth above.

Practical and presently preferred embodiments of the invention will be hereinafter explained in more detail referring to Production Examples, Formulation Examples and Test Examples. These examples, however, should not be construed to be limitative.

In the following Production Examples, % is by weight unless otherwise indicated.

Production Example 1 (Production of Compound No. 1)

A mixture of 0.30 g of potassium carbonate, 0.40 g of 2-chloro-4-sec-butoxyphenol, 0.32 g of p-chlorobenzyl chloride and 15 ml of N,N-dimethylformamide was stirred at room temperature overnight. The reaction mixture was poured into ice-water and extracted twice with 100 ml of ethyl acetate. The extracts were combined together, washed with water, dried over anhydrous magnesium sulfate and concentrated under reduced pressure. The residue was subjected to silica gel chromatography to give 0.51 g of 1-sec-butoxy-3-chloro-4-(4-chlorobenzyloxy)benzene. Yield, 78%. $n_D^{20.6}$ 1.5630.

Production Example 2 (Production of Compound No. 27)

A mixture of 0.30 g of potassium carbonate, 0.40 g of 2-chloro-4-sec-butoxyphenol, 0.28 g of p-methylbenzyl chloride and 15 ml of N,N-dimethylformamide was stirred at room temperature overnight. The reaction mixture was poured into ice-water and extracted twice with 100 ml of ethyl acetate. The extracts were combined together, washed with water, dried over anhydrous magnesium sulfate and concentrated under reduced pressure. The residue was subjected to silica gel chromatography to give 0.50 g of 1-sec-butoxy-3-chloro-4-(4-methylbenzyloxy)benzene. Yield, 82%. $n_D^{18.9}$ 1.5557.

Production Example 3 (Production of Compound No. 36)

A mixture of 0.30 g of potassium carbonate, 0.40 g of 2-chloro-4-sec-butoxyphenol, 0.37 g of p-fluorobenzyl bromide and 15 ml of N,N-dimethylformamide is stirred at room temperature overnight. The reaction mixture is poured into ice-water and extracted twice with 100 ml of ethyl acetate. The extracts are combined together, washed with water, dried over anhydrous magnesium sulfate and concentrated under reduced pressure. The residue is subjected to silica gel chromatography to give 1-sec-butoxy-3-chloro-4-(4-fluorobenzyloxy)benzene.

Production Example 4 (Production of Compound No. 2)

A mixture of 0.75 g of 2-chloro-4-(2-ethylbutyl)phenol, 0.50 g of p-chlorobenzyl alcohol, 0.92 g of triphenylphosphine, 0.71 g of diisopropylazadicarboxylate and 100 mg of tetrahydrofuran was stirred at room temperatur for 48 hours. The reaction mixture was concentrated, and 50 ml of diethyl ether was added thereto. The precipitates were removed by filtration, and the filtrate was concentrated. The residue was subjected to silica gel chromatography to give 0.75 g of 2-chloro-1-(4-chlorobenzyloxy)-4-(2-ethylbutyl)benzene. Yield, 63%. $n_D^{22.6}$ 1.5611.

Production Example 5 (Production of Compound No. 26)

A mixture of 0.74 g of 2-chloro-4-sec-butoxyphenol, 0.50 g of p-ethylbenzyl alcohol, 1.00 g of triphenylphosphine, 0.65 g of diethylazadicarboxylate and 100 mg of tetrahydrofuran was stirred at room temperatur for 48 hours. The reaction mixture was concentrated, and 50 ml of diethyl ether was added thereto. The precipitates were removed by filtration, and the filtrate was concentrated. The residue was subjected to silica gel chromatography to give 0.71 g of 1-sec-butoxy-3-chloro-4-(4-ethylbenzyloxy)-benzene. Yield, 60%. $n_D^{22.6}$ 1.5529.

Some examples of the aromatic compounds (I) as produced in the same manner as above are shown in Table 2.

TABLE 2

| Compound No. | Chemical structure | Physical constant |
|---|---|---|
| 1 | 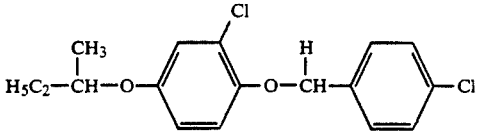 | $n_D^{20.6}$ 1.5630 |

TABLE 2-continued

| Compound No. | Chemical structure | Physical constant |
|---|---|---|
| 2 | H₅C₂-CH(C₂H₅)-CH₂-[C₆H₃(Cl)]-O-CH(H)-[C₆H₄]-Cl | $n_D^{22.6}$ 1.5611 |
| 3 | H₅C₂-CH(CH₃)-O-[C₆H₃(Cl)]-O-CH(H)-[C₆H₄]-Br | $n_D^{24.1}$ 1.5730 |
| 4 | H₅C₂-CH(CH₃)-O-[C₆H₃(Cl)]-O-CH(H)-[C₆H₃(F)]-F | $n_D^{18.5}$ 1.5372 |
| 5 | H₅C₂-CH(CH₃)-O-[C₆H₃(Cl)]-O-CH(H)-[C₆H₄]-I | $n_D^{18.7}$ 1.6013 |
| 6 | H₅C₂-CH(C₂H₅)-CH₂-[C₆H₃(Cl)]-O-CH(H)-[C₆H₄]-Br | $n_D^{23.4}$ 1.5723 |
| 7 | H₅C₂-CH(C₂H₅)-CH₂-[C₆H₃(Cl)]-O-CH(H)-[C₆H₃(F)]-F | $n_D^{24.0}$ 1.5724 |
| 8 | H₅C₂-CH(C₂H₅)-CH₂-[C₆H₃(Cl)]-O-CH(H)-[C₆H₄]-I | $n_D^{23.5}$ 1.5996 |
| 9 | H₃C-CH(CH₃)-CH₂-O-CH₂-[C₆H₃(Cl)]-O-CH(H)-[C₆H₄]-Cl | $n_D^{24.6}$ 1.5558 |
| 10 | H₅C₂-CH(CH₃)-O-[C₆H₃(Cl)]-O-CH(CH₃)-[C₆H₄]-Cl | $n_D^{24.5}$ 1.5479 |
| 11 | H₅C₂-CH(CH₃)-O-[C₆H₃(Cl)]-O-CH(H)-[C₆H₄]-F | $n_D^{22.7}$ 1.5462 |
| 12 | H₅C₂-CH(CH₃)-O-[C₆H₃(Cl)]-O-CH(H)-[C₆H₄]-Cl | $n_D^{22.7}$ 1.5570 |

TABLE 2-continued

| Compound No. | Chemical structure | Physical constant |
|---|---|---|
| 13 | $H_5C_2-CH(H)-O-\text{[2-Cl-phenyl-1,4]}-O-CH(H)-\text{[4-Cl-phenyl]}$ | $n_D^{23.0}$ 1.5730 |
| 14 | $H_7C_3-CH(H)-O-\text{[2-Cl-phenyl-1,4]}-O-CH(H)-\text{[4-Cl-phenyl]}$ | $n_D^{23.0}$ 1.5660 |
| 15 | $H_3C-CH(CH_3)-CH_2-O-\text{[2-Cl-phenyl-1,4]}-O-CH(H)-\text{[4-Cl-phenyl]}$ | $n_D^{24.4}$ 1.5630 |
| 16 | $H_9C_4-CH(H)-O-\text{[2-Cl-phenyl-1,4]}-O-CH(H)-\text{[4-Cl-phenyl]}$ | $n_D^{23.1}$ 1.5600 |
| 17 | $H_{11}C_5-CH(H)-O-\text{[2-Cl-phenyl-1,4]}-O-CH(H)-\text{[4-Cl-phenyl]}$ | $n_D^{23.2}$ 1.5555 |
| 18 | $H_5C_2-CH(CH_3)-CH_2-O-\text{[2-Cl-phenyl-1,4]}-O-CH(H)-\text{[4-Cl-phenyl]}$ | $n_D^{24.4}$ 1.5599 |
| 19 | $H_7C_3-CH(CH_3)-O-\text{[2-Cl-phenyl-1,4]}-O-CH(H)-\text{[4-Cl-phenyl]}$ | $n_D^{23.8}$ 1.5661 |
| 20 | $H_5C_2-CH(C_2H_5)-O-\text{[2-Cl-phenyl-1,4]}-O-CH(H)-\text{[4-Cl-phenyl]}$ | $n_D^{24.4}$ 1.5592 |
| 21 | $H_7C_3-CH(C_2H_5)-O-\text{[2-Cl-phenyl-1,4]}-O-CH(H)-\text{[4-Cl-phenyl]}$ | $n_D^{24.7}$ 1.5542 |
| 22 | $(CH_3)_2CH-CH(CH_3)-O-\text{[2-Cl-phenyl-1,4]}-O-CH(H)-\text{[4-Cl-phenyl]}$ | $n_D^{24.4}$ 1.5587 |
| 23 | $(CH_3)_2CH-CH(C_2H_5)-O-\text{[2-Cl-phenyl-1,4]}-O-CH(H)-\text{[4-Cl-phenyl]}$ | $n_D^{22.0}$ 1.5558 |

TABLE 2-continued

| Compound No. | Chemical structure | Physical constant |
|---|---|---|
| 24 | H₅C₂—CH(CH₃)—CH(CH₃)—O—[2-Cl-C₆H₃]—O—CH(H)—[4-Cl-C₆H₄] | $n_D^{21.8}$ 1.5565 |
| 25 | H₃C—CH(CH₃)—C₂H₄—O—[2-Cl-C₆H₃]—O—CH(H)—[4-Cl-C₆H₄] | $n_D^{24.4}$ 1.5582 |
| 26 | H₅C₂—CH(CH₃)—O—[2-Cl-C₆H₃]—O—CH(H)—[4-C₂H₅-C₆H₄] | $n_D^{20.6}$ 1.5529 |
| 27 | H₅C₂—CH(CH₃)—O—[2-Cl-C₆H₃]—O—CH(H)—[4-CH₃-C₆H₄] | $n_D^{18.9}$ 1.5557 |
| 28 | H₅C₂—CH(CH₃)—O—[2-Cl-C₆H₃]—O—CH(H)—[4-CF₃-C₆H₄] | $n_D^{18.4}$ 1.5191 |
| 29 | H₅C₂—CH(C₂H₅)—CH₂—[2-Cl-C₆H₃]—O—CH(H)—[4-CH₃-C₆H₄] | $n_D^{24.6}$ 1.5497 |
| 30 | H₅C₂—CH(C₂H₅)—CH₂—[2-Cl-C₆H₃]—O—CH(H)—[4-C₂H₅-C₆H₄] | $n_D^{23.9}$ 1.5479 |
| 31 | H₅C₂—CH(C₂H₅)—CH₂—[2-Cl-C₆H₃]—O—CH(H)—[4-CF₃-C₆H₄] | $n_D^{23.4}$ 1.5156 |
| 32 | H₃C—CH(CH₃)—CH₂OCH₂—[2-Cl-C₆H₃]—O—CH(H)—[4-CH₃-C₆H₄] | $n_D^{24.8}$ 1.5449 |
| 33 | H₃C—CH(CH₃)—CH₂OCH₂—[2-Cl-C₆H₃]—O—CH(H)—[4-C₂H₅-C₆H₄] | $n_D^{24.8}$ 1.5432 |
| 34 | H₅C₂—CH(CH₃)—O—[2-Cl-C₆H₃]—O—CH(H)—[3,4-methylenedioxyphenyl] | $n_D^{24.5}$ 1.5672 |

TABLE 2-continued

| Compound No. | Chemical structure | Physical constant |
|---|---|---|
| 35 | H₅C₂—CH(CH₃)—O—[2-Cl-phenyl]—O—CH(H)—[phenyl]—CH₂OCH₃ | $n_D^{24.5}$ 1.5509 |
| 36 | H₅C₂—CH(CH₃)—O—[2-Cl-phenyl]—O—CH(H)—[phenyl]—F | |

A typical embodiment for production of the intermediary compound (II) is shown below.

Production Example 6 (Production of the compound (IV), i.e. 4-sec-butoxy-2-chlorophenol)

To a solution of 5.0 g of 4-sec-butoxyphenol in 50 ml of carbon tetrachloride, there was added dropwise 3.27 g of t-butylhypochlorite with vigorously stirring and ice-cooling. After completion of the addition, the reaction mixture was stirred at room temperature for 5 hours and concentrated, followed by addition of 200 ml of ethyl acetate. The obtained solution was washed with an agueous solution of 5% wt. sodium dicarbonate, dried and concentrated under reduced pressure. The residue was subjected to silica gel chromatography to give 5.32 g of 4-sec-butoxy-2-chlorophenol. Yield. 88%. $n_D^{23.5}$ 1.5312.

Some examples of the intermediary compound (II) as produced in the same manner as above are shown in Table 3.

TABLE 3

| Compound No. | Chemical structure | Physical constant |
|---|---|---|
| 101 | H₅C₂—CH(CH₃)—O—[2-Cl-phenyl]—OH | $n_D^{23.5}$ 1.5312 |
| 102 | H₃C—CH(CH₃)—CH₂OCH₂—[2-Cl-phenyl]—OH | $n_D^{22.0}$ 1.5266 |
| 103 | H₅C₂—CH(C₂H₅)—CH₂—[2-Cl-phenyl]—OH | $n_D^{22.0}$ 1.5240 |

In Formulation Examples as set forth below, parts and % are all by weight. The compound numbers correspond to those as shown in Table 2.

Formulation Example 1 (Emulsifiable concentrate)

To a solution of 10 parts of each of Compounds Nos. 1 to 36 in 35 parts of xylene and 35 parts of dimethylformamide, 14 parts of polyoxyethylene styrylphenyl ether and 6 parts of calcium dodecylbenzenesulfonate are added, and the resultant mixture is thoroughly mixed while stirring to give an emulsifiable concentrate containing the active ingredient in 10%.

Formulation Example 2 (Wettable powder)

Twenty parts of each of Compounds Nos. 1 to 36 are added to a mixture of 4 parts of sodium laurylsulfate, 2 parts of calcium ligninsulfonate, 20 parts of fine powders of synthetic hydrated silica and 54 parts of diatomaceous earth, and the resultant mixture is stirred in a mixer to give a wettable powder containing the active ingredient in 20%.

Formulation Example 3 (Granules)

Five parts of sodium dodecylbenzenesulfonate, 30 parts of bentonite and 60 parts of clay are added to 5 parts of each of Compound Nos. 1 to 36, and the resultant mixture is pulverized and kneaded with a suitable amount of water. The mixture is granulated in a granulator and air-dried to give granules containing the active ingredient in 5%.

Formulation Example 4 (Dusts)

To a mixture of 1 part of fine powders of synthetic hydrated silica, 1 part of an aggregating agent ("Driless B" manufactured by Sankyo Co., Ltd.) and 7.7 parts of clay, 0.3 part of each of Compound Nos. 1 to 36 is added, and the resultant mixture is well pestled in a mortar and further stirred in a mixer. To the thus obtained mixture, there are added 90 parts of cut clay, followed by mixing to give dusts containing the active ingredient in 0.3%.

Formulation Example 5 (Dusts)

A mixture of 0.3 part of each of Compound Nos. 1 to 36, 2 parts of fenitrothion (O,O-dimethyl O-(3-methyl-4-nitrophenyl)phosphorothioate as an organophosphorus insecticide, 3 parts of fine powders of synthetic hydrated silica, 1 part of "Driless B" and 3.7 parts of clay are pestled in a mortar and stirred in a mixer. Then, 90 parts of cut clay are added thereto, and the resultant mixture is further mixed in a sack to give dusts.

Formulation Example 6 (Dusts)

A mixture of 0.3 part of each of Compound Nos. 1 to 36, 2 parts of BPMC (O-sec-butylphenyl N-methylcarbamate) as a carbamate insecticide, 3 parts of fine powders of synthetic hydrated silica, 1 part of "Driless B" and 3.7 parts of clay are pestled in a mortar and stirred in a mixer. Then, 90 parts of cut clay are added thereto, and the resultant mixture is further mixed in a sack to give dusts.

Formulation Example 7 (Dusts)

To a solution of 1 part of each of Compound Nos. 1 to 36 in an appropriate amount of acetone, 5 parts of fine powders of synthetic hydrated silica, 0.3 part of PAP (acidic isopropyl phosphate) and 93.7 parts of clay are added, and the resultant mixture is stirred in a mixer, followed by evaporation of acetone to give dusts containing the active ingredient in 1%.

Formulation Example 8 (Flowable concentrate)

To 40 parts of an aqueous solution containing 2 parts of polyvinyl alcohol, 10 parts of each of Compound Nos. 1 to 36 are added, and the resultant mixture is stirred in a mixer. To the thus obtained dispersion, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate containing the active ingredient in 10%.

Formulation Example 9 (Oil spray)

Into a mixture of 5 parts of xylene and 5 parts of trichloroethane, 0.1 part of each of Compound Nos. 1 to 36 is dissolved, and the resultant solution is mixed with 89.9 parts of deodorized kerosene to give an oil spray containing the active ingredient in 0.1%.

Formulation Example 10 (Oil-based aerosol)

A solution of 0.1 part of each of Compound Nos. 1 to 36, 0.2 part of tetramethrin (2,2-dimethyl-3-(2-methyl-1-propenyl)cyclopropanecarboxylic acid (1,2,3,4,5,7-hexahydro-1,3-dioxo-2H-isoindol-2-yl)methyl ester) and 0.1 part of d-phenothrin (2,2-dimethyl-3-(2-methyl-1-propenyl)cyclopropanecarboxylic acid (3-phenoxyphenyl)methyl ester) in a mixture of 10 parts of trichloroethane and 59.6 parts of deodorized kerosene is filled in an aerosol container. After provision of a valve, 30 parts of a propellant (liquefied petroleum gas) is filled through the valve under reduced pressure to give an oil-based aerosol.

Formulation Example 11 (Water-based aerosol)

A solution of 0.2 part of each of Compound Nos. 1 to 36, 0.2 part of d-allethrin ((2,2-dimethyl-3-(2-methyl-1-propenyl)cyclopropanecarboxylic acid 2-methyl-4-oxo-3-(2-propenyl)-2-cyclopenten-2-yl ester), 0.2 part of d-phenothrin, 5 parts of xylene, 3.4 parts of deodorized kerosene and 1 part of an emulsifier ("ATMOS 300" ®, Atlas Chemical Co., Ltd.) in 50 parts of distilled water is filled in an aerosol container. After provision of a valve, 40 parts of a propellant (liquefied petroleum gas) is filled through the valve under reduced pressure to give a water-based aerosol.

Formulation Example 12 (Fumigant)

Each of Compound Nos. 1 to 36 (100 mg) is dissolved in an appropriate amount of acetone, and the resultant solution is impregnated with a porous ceramic plate (4.0×4.0×1.2 cm) to give a fumigant.

The following Test Examples show some of test results which support the controlling effect of the aromatic compounds (I) on insect pests. The compound numbers correspond to those as shown in Table 2. The compounds used for comparison are as follows:

| Compound symbol | Chemical structure | Remarks |
|---|---|---|
| A | 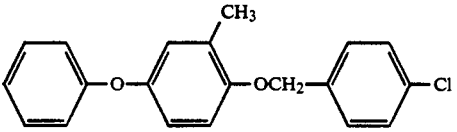 | Compound disclosed in U.S. Pat. No. 3,987,102 |

Test Example 1

Metamorphosis inhibitory activity against brown rice planthopper nymphs

An emulfiable concentrate prepared according to Formulation Example 1 was diluted with water to make a predetermined concentration. The dilution was sprayed onto rice plants cultivated in polyethylene cups at a rate of 20 ml/2 pots on a turning table. After air-drying, the plants were infested with about ten 3rd instar nymphs of brown rice planthopper (*Nilaparvata lugens*). After 10 days, the number of normal adults was counted to obtain an emergence inhibitory rate. The results are shown in Table 4.

TABLE 4

| Compound No. | Concentration (ppm) | Inhibitory rate (%) |
|---|---|---|
| 1 | 50 | 100 |
|  | 5 | 100 |
| 2 | 50 | 100 |
|  | 5 | 100 |
| 3 | 50 | 100 |
|  | 5 | 100 |
| 4 | 50 | 100 |
|  | 5 | 100 |
| 5 | 50 | 100 |
|  | 5 | 100 |
| 6 | 50 | 100 |
|  | 5 | 100 |
| 7 | 50 | 100 |
|  | 5 | 100 |
| 8 | 50 | 100 |
|  | 5 | 100 |
| 9 | 50 | 100 |
|  | 5 | 100 |
| 10 | 50 | 100 |
|  | 5 | 100 |
| 11 | 50 | 100 |
|  | 5 | 100 |
| 12 | 50 | 100 |
|  | 5 | 100 |
| 13 | 50 | 100 |
|  | 5 | 100 |
| 14 | 50 | 100 |
|  | 5 | 100 |
| 15 | 50 | 100 |
|  | 5 | 100 |
| 16 | 50 | 100 |
|  | 5 | 100 |
| 17 | 50 | 100 |
|  | 5 | 100 |
| 18 | 50 | 100 |
|  | 5 | 100 |

TABLE 4-continued

| Compound No. | Concentration (ppm) | Inhibitory rate (%) |
| --- | --- | --- |
| 19 | 50 | 100 |
|    | 5  | 100 |
| 20 | 50 | 100 |
|    | 5  | 100 |
| 21 | 50 | 100 |
|    | 5  | 100 |
| 22 | 50 | 100 |
|    | 5  | 100 |
| 23 | 50 | 100 |
|    | 5  | 100 |
| 24 | 50 | 100 |
|    | 5  | 100 |
| 25 | 50 | 100 |
|    | 5  | 100 |
| 26 | 50 | 100 |
|    | 5  | 100 |
| 27 | 50 | 100 |
|    | 5  | 100 |
| 28 | 50 | 100 |
|    | 5  | 100 |
| 29 | 50 | 100 |
|    | 5  | 100 |
| 30 | 50 | 100 |
|    | 5  | 100 |
| 31 | 50 | 100 |
|    | 5  | 100 |
| 32 | 50 | 100 |
|    | 5  | 100 |
| 33 | 50 | 100 |
|    | 5  | 100 |
| 34 | 50 | 100 |
|    | 5  | 100 |
| 35 | 50 | 100 |
|    | 5  | 100 |
| A  | 50 | 25 |

Compound Nos. 1, 2, 3, 5, 6, 8, 9, 12, 13, 19 and 26 to 33 showed a 100% emergence inhibition at a concentration of 500 ppb.

Test Example 2

Reproduction inhibitory activity against green rice leafhopper

An emulfiable concentrate prepared according to Formulation Example 1 was diluted with water to make a predetermined concentration. The dilution was sprayed onto rice plants (about 20 cm in height) cultivated in plastic pots (1/5000 are in width) at a rate of 40 ml/2 pots on a turning table. After air-drying, the pots were covered with wire cages, and each 10 male and female adults of green rice leafhopper (*Nephotettix cincticeps*) were released in each of the cages. After 3 weeks, the number of nymphs was counted to obtain a reproduction inhibitory rate. The results are shown in Table 5.

TABLE 5

| Compound No. | Concentration (ppm) | Inhibitory rate (%) |
| --- | --- | --- |
| 1  | 100 | 100 |
| 26 | 100 | 98  |
| 27 | 100 | 99  |
| A  | 100 | 0   |

Test Example 3

Reproduction inhibitory activity against brown rice planthopper

An emulfiable concentrate prepared according to Formulation Example 1 was diluted with water to make a predetermined concentration. The dilution was sprayed onto rice plants (about 20 cm in height) cultivated in plastic pots (1/5000 are in width) at a rate of 40 ml/2 pots on a turning table. After air-drying, the pots were covered with wire cages, and each 5 male and female adults of brown rice planthopper (*Nilaparvata lugens*) were released in each of the cages. After about 3 weeks, the number of nymphs was counted to obtain a reproduction inhibitory rate. The results are shown in Table 6.

TABLE 6

| Compound No. | Concentration (ppm) | Ovicidal rate (%) |
| --- | --- | --- |
| 1  | 100 | 100 |
| 26 | 100 | 95  |
| 27 | 100 | 97  |
| A  | 100 | 0   |

Test Example 4

Reproduction inhibitory activity against cotton aphids

An emulfiable concentrate prepared according to Formulation Example 1 was diluted with water to make a predetermined concentration. The dilution was sprayed onto potted cotton plants (in a stage of 8–9 days after sowing) infested with 1st instar nymphs of cotton aphids (*Aphis gossypii*) at a rate of 30 ml/2 pots on a turning table. Before spraying and one week after spraying, the humber of nymphs and aduts was counted, and a reproduction inhibitory index was expressed by the following equation:

$$\text{Reproduction inhibitory index} = \frac{\text{Number of individuals one week after spraying per 2 pots}}{\text{Number of individuals before spraying per 2 pots}}$$

wherein the judgement of activity is based on the following standard:
A: less than 1 (excellent effect)
B: from 1 to 3 (slight effect)
C: more than 3 (little effect)
D: same as in the untreated pots (no effect)
The results are shown in Table 7.

TABLE 7

| Compound No. | Concentration (ppm) | Inhibitory rate |
| --- | --- | --- |
| 26 | 10 | A |
| 27 | 10 | A |
| 29 | 10 | A |
| A  | 10 | D |

What is claimed is:

1. A method for controlling insect pests which comprises applying as the active ingredient an effective amount of an aromatic compound of the formula:

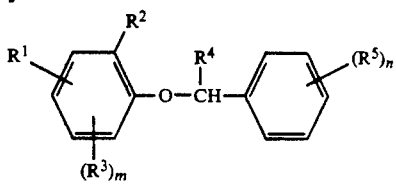

wherein $R^1$ is a $C_3$–$C_8$ alkyl group, a $C_3$–$C_8$ alkoxy group, an alkoxyalkyl group having 3 to 8 carbon atoms, a $C_3$-$C_8$ alkenyl group, a $C_3$-$C_8$ alkenyloxy group, an alkenyloxyalkyl group having 3 to 8 carbon atoms, a $C_3$-$C_8$ haloalkyl group, a $C_3$-$C_8$ haloalkoxy group, a haloalkoxyalkyl group having 3 to 8 carbon atoms, a $C_3$-$C_8$ haloalkenyl group, a $C_3$-$C_8$ haloalkenyloxy group, a haloalkenyloxyalkyl group having 3 to 8 carbon atoms or a $C_3$-$C_8$ alkynyloxy group; $R^2$ is a halogen atom; $R^3$ is, the same or different, a hydrogen atom, a halogen atom or a methyl group; $R^4$ is a hydrogen atom or a methyl group; $R^5$ is, the same or different, a hydrogen atom, a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group, a $C_1$-$C_4$ haloalkylthio group, a 3,4-methylenedioxy group, a methoxymethyl group, a cyano group or a nitro group; m is an integer of 1 to 3; and n is an integer of 1 to 5, to the insect pests or the locus where the insect pests propagate.

2. The method according to claim 1, which comprises applying the aromatic compound as defined in claim 1 wherein $R^2$ is a chlorine atom.

3. The method according to claim 1, which comprises applying the aromatic compound as defined in claim 1 wherein $R^2$ is a chlorine atom and $R^5$ is, the same or different, a halogen atom and n is an integer of 1 to 5.

4. The method according to claim 1, which comprises applying the aromatic compound as defined in claim 1 wherein $R^2$ is a chlorine atom, $R^5$ is an ethyl group and n is an integer of 1 to 5.

5. The method according to claim 1, which comprises applying any one of the aromatic compounds as defined in claim 1 selected from the following group: 1-sec-butoxy-3-chloro-4-(4-chlorobenzyloxy)benzene; 1-sec-butoxy-4-(4-bromobenzyloxy)-3-chlorobenzene; 1-sec-butoxy-3-chloro-4-(4-iodobenzyloxy)benzene; 1-sec-butoxy-3-chloro-4-(4-ethylbenzyloxy)benzene; 1-sec-butoxy-3-chloro-4-(4-methylbenzyloxy)benzene; 1-sec-butoxy-3-chloro-4-(4-trifluoromethylbenzyloxy)benzene; 3-chloro-4-(4-chlorobenzyloxy)-1-isobutoxymethylbenzene; 3-chloro-4-(4-chlorobenzyloxy)-1-(2-ethylbutyl)benzene; 3-chloro-4-(4-chlorobenzyloxy)-1-(1-methylbutoxy)benzene; 1-sec-butoxy-3-chloro-4-(3,4-difluorobenzyloxy)benzene; 1-sec-butoxy-3-chloro-4-[1-(4-chlorophenyl)ethyloxy]benzene; 1-sec-butoxy-3-chloro-4-(3-chlorobenzyloxy)benzene; 3-chloro-1-(2-ethylbutyl)-4-(4-methylbenzyloxy)benzene; and 3-chloro-1-isobutoxymethyl-4-(4-methylbenzyloxy)benzene.

6. The method according to claim 1, which comprises applying 1-sec-butoxy-3-chloro-4-(4-chlorobenzyloxy)benzene as the aromatic compound defined in claim 1.

7. The method according to claim 1, which comprises applying 1-sec-butoxy-3-chloro-4-(4-ethylbenzyloxy)benzene as the aromatic compound defined in claim 1.

8. The method according to claim 1, which comprises applying 1-sec-butoxy-3-chloro-4-(4-methylbenzyloxy)benzene as the aromatic compound defined in claim 1.

* * * * *